US012296002B2

(12) United States Patent
Kuo et al.

(10) Patent No.: US 12,296,002 B2
(45) Date of Patent: May 13, 2025

(54) IMMUNOGENIC COMPOSITION AGAINST SEVERE ACUTE RESPIRATORY SYNDROME CORONAVIRUS 2 (SARS-CoV-2)

(71) Applicants: Medigen Vaccine Biologics Corporation, Zhubei (TW); Dynavax Technologies Corporation, Emeryville, CA (US)

(72) Inventors: Tsun-Yung Kuo, I-Lan County (TW); Charles Chen, Taipei (TW); Chung-Chin Wu, I-Lan County (TW); Yi-Jiun Lin, Taipei (TW); Meei-Yun Lin, Taipei (TW); Yu-Chi Wu, Taipei (TW); John Darren Campbell, Emeryville, CA (US); Robert S. Janssen, Emeryville, CA (US); David Novack, Emeryville, CA (US); Robert Coffman, Emeryville, CA (US); Paula Traquina, Emeryville, CA (US)

(73) Assignees: MEDIGEN VACCINE BIOLOGICS CORPORATION, Zhubei (TW); DYNAVAX TECHNOLOGIES CORPORATION, Emeryville, CA (US)

( * ) Notice: Subject to any disclaimer, the term of this patent is extended or adjusted under 35 U.S.C. 154(b) by 833 days.

(21) Appl. No.: 17/351,363

(22) Filed: Jun. 18, 2021

(65) Prior Publication Data

US 2021/0308257 A1    Oct. 7, 2021

Related U.S. Application Data

(63) Continuation of application No. PCT/US2021/020277, filed on Mar. 1, 2021.
(Continued)

(51) Int. Cl.
*A61K 39/215* (2006.01)
*A61P 31/14* (2006.01)
(Continued)

(52) U.S. Cl.
CPC ............ *A61K 39/215* (2013.01); *A61P 31/14* (2018.01); *C07K 14/005* (2013.01);
(Continued)

(58) Field of Classification Search
None
See application file for complete search history.

(56) References Cited

U.S. PATENT DOCUMENTS 6,309,650 B1   10/2001   Kim et al.
6,589,940 B1   7/2003   Raz et al.
(Continued)

FOREIGN PATENT DOCUMENTS

CN    1827936 A    9/2006
CN    101240271 A   8/2008
(Continued)

OTHER PUBLICATIONS

SEQ 1 alignment with Geneseq db access BJY36088 Mar. 25, 2020.*
(Continued)

*Primary Examiner* — Shanon A. Foley
(74) *Attorney, Agent, or Firm* — troutman pepper locke; Tim Tingkang Xia, Esq.

(57) ABSTRACT

The present invention relates to an immunogenic composition against severe acute respiratory syndrome coronavirus 2 (SARS-CoV-2), especially to an immunogenic composition having a recombinant SARS-CoV-2 S protein and adjuvant.

14 Claims, 13 Drawing Sheets

Specification includes a Sequence Listing.

Related U.S. Application Data

(60) Provisional application No. 63/040,696, filed on Jun. 18, 2020, provisional application No. 62/983,737, filed on Mar. 1, 2020.

(51) Int. Cl.
*C07K 14/005* (2006.01)
*C07K 14/165* (2006.01)
*C07K 14/245* (2006.01)
*A61K 39/00* (2006.01)

(52) U.S. Cl.
CPC .......... *C07K 14/165* (2013.01); *C07K 14/245* (2013.01); *A61K 2039/54* (2013.01); *A61K 2039/545* (2013.01); *A61K 2039/55505* (2013.01); *A61K 2039/55561* (2013.01); *A61K 2039/575* (2013.01); *C07K 2319/33* (2013.01); *C12N 2770/20022* (2013.01); *C12N 2770/20034* (2013.01); *C12N 2770/20071* (2013.01); *C12N 2795/10022* (2013.01); *C12N 2795/10034* (2013.01); *C12N 2795/10071* (2013.01)

(56) References Cited

U.S. PATENT DOCUMENTS

| | | | |
|---|---|---|---|
| 10,953,089 B1 | 3/2021 | Smith et al. | |
| 11,213,482 B1 | 1/2022 | Gambotto et al. | |
| 11,684,669 B2 | 6/2023 | Meinke et al. | |
| 2006/0257852 A1 | 11/2006 | Rappuoli et al. | |
| 2007/0116716 A1 | 5/2007 | Shen et al. | |
| 2008/0305120 A1* | 12/2008 | Messmer | A61P 35/04 435/252.8 |
| 2009/0017069 A1 | 1/2009 | Akeefe et al. | |
| 2009/0104229 A1 | 4/2009 | Voss | |
| 2011/0052621 A1 | 3/2011 | Champion et al. | |
| 2012/0121630 A1* | 5/2012 | Bryan | A61K 39/245 435/69.3 |
| 2015/0125475 A1* | 5/2015 | Dodd | A61P 37/04 546/10 |
| 2017/0246281 A1 | 8/2017 | Super et al. | |
| 2019/0134190 A1 | 5/2019 | Rittner et al. | |
| 2021/0139543 A1 | 5/2021 | He | |
| 2021/0260181 A1 | 8/2021 | Georges et al. | |
| 2021/0308257 A1 | 10/2021 | Kuo et al. | |
| 2023/0038284 A1 | 2/2023 | Meinke et al. | |
| 2023/0092650 A1 | 3/2023 | Campbell et al. | |
| 2023/0110516 A1 | 4/2023 | Campbell et al. | |
| 2023/0218740 A1 | 7/2023 | Campbell et al. | |
| 2023/0346915 A1 | 11/2023 | Goodrich et al. | |

FOREIGN PATENT DOCUMENTS

| | | |
|---|---|---|
| CN | 102068692 A | 5/2011 |
| CN | 111218458 A | 6/2020 |
| EP | 2484378 A1 | 8/2012 |
| WO | 200020039 A1 | 4/2000 |
| WO | 200062802 A2 | 10/2000 |
| WO | 200062802 A3 | 1/2001 |
| WO | 200100232 A2 | 1/2001 |
| WO | 200100232 A3 | 5/2001 |
| WO | 2003011334 A1 | 2/2003 |
| WO | 2004092360 A2 | 10/2004 |
| WO | 2004094614 A2 | 11/2004 |
| WO | 2004092360 A3 | 8/2005 |
| WO | 2005111238 A2 | 11/2005 |
| WO | 2005111238 A3 | 5/2006 |
| WO | 2004094614 A3 | 7/2006 |
| WO | 2007122392 A1 | 11/2007 |
| WO | 2013083726 A1 | 6/2013 |
| WO | 2014153087 A1 | 9/2014 |
| WO | 2016203025 A1 | 12/2016 |
| WO | 2017109223 A1 | 6/2017 |
| WO | 2017109225 A1 | 6/2017 |
| WO | 2018081318 A1 | 5/2018 |
| WO | 2018147265 A1 | 8/2018 |
| WO | 2018200645 A1 | 11/2018 |
| WO | 2019057793 A1 | 11/2018 |
| WO | 2021048221 A1 | 3/2021 |
| WO | 2021176434 A1 | 9/2021 |
| WO | 2021178318 A1 | 9/2021 |
| WO | 2021178321 A1 | 9/2021 |
| WO | WO 2021/178661 * | 9/2021 |
| WO | 2021178877 A1 | 12/2021 |
| WO | 2021204825 A2 | 12/2021 |
| WO | 2021254473 A1 | 12/2021 |

OTHER PUBLICATIONS

Alignment of SEQ 2 with UniProt db access M1E1E4_9HIV1 2014.*
Alignment of SEQ ID No. 5 with Geneseq db access BKD68505 by Henderson Apr. 14, 2020.*
Abdullah, S.F. et al. (2020, e-pub. Jun. 30, 2020). "SARS-CoV-2: A Piece of Bad News," Medeniyet Med. J. 35(2):151-160.
Afrough, B. et al. (May 2019). "Emerging Viruses and Current Strategies For Vaccine Intervention," Clin Exp. Immunol. 196(2):157-166.
Agrawal, A.S. et al. (2016, e-pub. Jun. 7, 2016). "Immunization with Inactivated Middle East Respiratory Syndrome Coronavirus Vaccine Leads to Lung Immunopathology on Challenge with Live Virus," Human Vaccines & Immunotherapeutics 12(9):2351-2356.
Ahmed, S.F. et al. (2020, e-pub. Feb. 25, 2020). "Preliminary Identification of Potential Vaccine Targets for the COVID-19 Coronavirus (SARS-CoV-2) Based on SARS-CoV Immunological Studies," Viruses 12(3):254, 15 pages.
Amanat, F. et al. (Jul. 16, 2020). "A Serological Assay To Detect SARS-CoV-2 Seroconversion In Humans," MedRxiv, Jan. 26, 2012.
Anonymous (2021). "What's in Vaccines?," The Center for Disease Control and Prevention, 2 pages.
Anonymous (Jan. 30, 2020). "Novel Coronavirus (2019-nCOV), Situation Report 10," World Health Organization, 7 pages.
Anonymous (Jun. 24, 2022). "Valneva Receives Marketing Authorization in Europe for Inactivated Whole-Virus COVID-19 Vaccine VLA2001," Valneva Press Release, 4 pages.
Arunachalam, P.S. et al. (2021, e-pub. Apr. 19, 2021). "Adjuvanting a Subunit COVID-19 Vaccine To Induce Protective Immunity," Nature 594:253-258, 27 pages.
Bao, L. et al. (Mar. 4, 2020), "Reinfection Could Not Occur In SARS-Co V-2 Infected Rhesus Macaques," BioRxiv, 20 pages.
Bao, M. et al. (2006, e-pub. Nov. 17, 2005). "Anti-SARS-CoV Immunity Induced by a Novel CpG Oligodeoxynucleotide," Clinical Immunology 118:180-187.
Berger, A. (Aug. 12, 2000). Th1 and Th2 Responses: What Are They? BMJ. 321(7258):424, 1 page.
Bode, C. et al. (Apr. 2011). "CpG DNA as a Vaccine Adjuvant," Expert Rev Vaccines 10(4):499-511, author manuscript, 22 pages.
Braun, R.P. et al. (Sep. 15, 1988). "Immunogenic Duplex Nucleic Acids Are Nuclease Resistant," J Immunol. 141(6):2084-2089.
Callaway, E. (Apr. 2020). "The Race for Coronavirus Vaccines: A Graphical Guide," Nature 580(7805):576-577.
Campbell, J.D. (2017). "Chapter 2: Development of The CpG Adjuvant 1018: A Case Study," Methods Mol Biol. 1494:15-27.
Capobianchi, M.R. et al. (2020, e-pub. Mar. 27, 2020). "Molecular Characterization of SARS-CoV-2 From The First Case of COVID-19 in Italy," Clin. Microbial Infect. 26(7):954-956.
Chan, J.F.-W. et al. (2020, e-pub. Jan. 28, 2020). "Genomic Characterization of the 2019 Novel Human-Pathogenic Coronavirus Isolated From a Patient With Atypical Pneumonia After Visiting Wuhan," Emerging Microbes & Infections 9(1):221-236.
Chen, Y. et al. (2020, e-pub. Feb. 17, 2020). "Structure Analysis of the Receptor Binding of 2019-nCoV," Biochemical and Biophysical Research Communications 525:135-140.
Chuang, T.-H. et al. (Mar. 2002). "Toll-Like Receptor 9 Mediates CpG-DNA Signaling," J Leukoc Biol. 71(3):538-544.

(56) References Cited

OTHER PUBLICATIONS

Coffman, R.L. et al. (Oct. 29, 2010) "Vaccine Adjuvants: Putting Innate Immunity to Work," Immunity 33(4):492-503, author manuscript, 21 pages.
Darnell, M.E.R. et al. (2004, e-pub. Aug. 3, 2004). "Inactivation of The Coronavirus That Induces Severe Acute Respiratory Syndrome, SARS-CoV," J. Virol. Methods 121(1):85-91.
Deng, Y. et al. (2018, e-pub. Apr. 4, 2018). "Enhanced Protection in Mice Induced By Immunization With Inactivated Whole Viruses Compare to Spike Protein of Middle East Respiratory Syndrome Coronavirus," Emerging Microbes & Infections 7(1):60, 11 pages.
Devereux, J. et al. (1984). "A Comprehensive Set Of Sequence Analysis Programs For The VAX," Nucleic Acids Research 12(1):387-395.
Draper, S.J. et al. (Jul. 11, 2018). "Malaria Vaccines: Recent Advances and New Horizons," Cell Host Microbe 24(1):43-56.
Du, L. et al. (2009, e-pub. Feb. 9, 2009). "The Spike Protein of SARS-CoV-a Target For Vaccine and Therapeutic Development," Nature Reviews Microbiology, 7:226-236.
Enjuanes, L. et al. (2016, e-pub. Aug. 30, 2016). "Molecular Basis of Coronavirus Virulence and Vaccine Development," Adv. Virus Res. 96:245-286, 31 pages.
Excler, J.-L. et al. (2021, e-pub. Apr. 12, 2021). "Vaccine Development For Emerging Infectious Diseases," Nat Med. 27(4):591-600.
Hyer, R. et al. (2019, e-pub. Aug. 17, 2019). "Immunogenicity and Safety of a 2-Dose Hepatitis B Vaccine, HBsAg/CpG 1018, in Persons with Diabetes Mellitus Ages 60-70 Years," Vaccine 37(39):5854-5861.
Ferguson, N.M. et al. (Mar. 16, 2020). "Report 9: Impact of Non-Pharmaceutical Interventions (NPIs) To Reduce COVID-19 Mortality and Healthcare Demand," Imperial College London, 20 pages.
Francica, J.R. et al. (Nov. 28, 2017). "Innate Transcriptional Effects By Adjuvants On The Magnitude, Quality and Durability of HIV Envelope Responses In NHPs," Blood Adv. 1(25):2329-2342.
Frieman, M. et al. (2012, e-pub. Nov. 9, 2011). "Molecular Determinants Of Severe Acute Respiratory Syndrome Coronavirus Pathogenesis and Virulence In Young and Aged Mouse Models Of Human Disease," J. Virol. 86(2):884-897.
Gao, Q. et al. (2020, e-pub. May 6, 2020). "Development of an Inactivated Vaccine Candidate For SARS-CoV-2," Science 369(6499):77-81, 5 pages.
GENBANK Submission; NIH/NCBI, Accession No. MN908947.3. Wu et al., Mar. 18, 2020, 11 pages.
GENBANK Submission; NIH/NCBI, Accession No. MT066156.1 Capobianchi et al., Apr. 13, 2020, 11 pages.
Glass, W.G. et al. (Sep. 15, 2004). "Mechanisms of Host Defense Following Severe Acute Respiratory Syndrome-Coronavirus (SARS-CoV) Pulmonary Infection of Mice," J. Immunol. 173(6):4030-4039.
Graham, B.S. et al. (2018, e-pub. Dec. 14, 2017). "Emerging Viral Diseases From a Vaccinology Perspective: Preparing For The Next Pandemic," Nat Immunol. 19(1):20-28.
Graham, R.L. et al. (2013, e-pub. Nov. 11, 2013). "A Decade After SARS: Strategies For Controlling Emerging Coronaviruses," Nature Reviews Microbiology, 11:836-848.
Gupta, D. et al. (2021, e-pub. Apr. 23, 2021). "Inactivation of SARS-COV-2 by β-propiolactone Causes Aggregation of Viral Particles and Loss of Antigenic Potential," 305:198555, 9 pages.
Han, Q. et al. (2020, e-pub. Feb. 11, 2020). "Coronavirus 2019-nCoV: A Brief Perspective From The Front Line," J Infect. 80(4):373-377.
He, Y. et al. (2004, e-pub. Oct. 28, 2004). "Inactivated SARS-CoV Vaccine Elicits High Titers of Spike Protein-Specific Antibodies That Block Receptor Binding and Virus Entry," Biochem. Biophys. Res. Commun. 325(2):445-452.
Henikoff, S. et al. (Nov. 15, 1992). "Amino Acid Substitution Matrices From Protein Blocks," Proc. Nat'l Acad. Sci. USA 89:10915-10919.

Herrera-Rodriguez, J. et al. (2019, e-pub. Feb. 11, 2019). "Inactivated or Damages? Comparing the Effect of Inactivation Methods on Influenza Virions to Optimize Vaccines Production," Vaccine 37(12):1630-1637.
Hogan, R.J. et al. (Oct. 2004). "Resolution of Primary Severe Acute Respiratory Syndrome-Associated Coronavirus Infection Requires Stat1," J. Virol. 78(20):11416-11421.
Hombach, J. et al. (2005, e-pub. Jul. 18, 2005). "Report on a WHO Consultation On Immunological Endpoints For Evaluation of New Japanese Encephalitis Vaccines, WHO, Geneva, Sep. 2-3, 2004," Vaccine. 23(45):5205-5211.
Hotez, P.J. et al. (Jul. 2020). "COVID-19 Vaccines: Neutralizing Antibodies and The Alum Advantage," Nat. Rev. Immunol. 20(7):399-400.
Huh, K. et al. (Mar. 2020). "Emergent Strategies for the Next Phase of COVID-19," Infect Chemother. 52(1):105-109.
Ioannou, X.P. et al. (Nov. 22, 2002). "CpG-Containing Oligodeoxynucleotides, In Combination With Conventional Adjuvants, Enhance The Magnitude and Change The Bias Of The Immune Responses To a Herpesvirus Glycoprotein," Vaccine 21(1-2):127-137.
Jureka, A.S. et al. (Jun. 6, 2020). "Propagation, Inactivation, and Safety Testion of SARS-CoV-2," Viruses 12(6):622, 13 pages.
Khan, J. et al. (Apr. 2020). "We've Never Made a Successful Vaccine For a Coronavirus Before. This Is Why It's So Difficult," ABC Health and Wellbeing, retrieved from the Internet https://www.abc.net.au/news/health/2020-04-17/coronavirus-vaccine-ian-frazer/12146616, last visited Sep. 20, 2021, 6 pages.
Wang, S.-F. et al. (2014, e-pub. Jul. 26, 2014). "Antibody-Dependent SARS Coronavirus Infection Is Mediated By Antibodies Against Spike Proteins," Biochem. Biophys. Res. Commun. 451(2):208-214.
Wang, Z.-B. et al. (Mar. 13, 2020). "Better Adjuvants For Better Vaccines: Progress In Adjuvant Delivery Systems, Modifications, and Adjuvant-Antigen Codelivery," Vaccines (Basel). 8(1):128, 20 pages.
Wrapp, D. et al. (2020, e-pub. Feb. 19, 2020). "Cryo-EM Structure of the 2019-nCoV Spiked in the Prefusion Conformation," Science 367:1260-1263.
Wu, F. et al. (2020, e-pub Feb. 3, 2020). "A New Coronavirus Associated with Human Respiratory Disease in China," Nature 579(7798):265-269, 20 pages.
Wu, Z. et al. (Apr. 7, 2020). "Characteristics of and Important Lessons From The Coronavirus Disease 2019 (COVID-19) Outbreak In China: Summary Of a Report of 72 314 Cases From The Chinese Center For Disease Control and Prevention," JAMA. 323(13):1239-1242.
Zakhartchouk, A.N. et al. (2007, e-pub. Aug. 2, 2008). "Immunogenicity of a Receptor-Binding Domain of SARS Coronavirus Spike Protein in Mice: Implications for a Subunit Vaccine," Vaccine 25:136-143.
Zeng, W. et al. (2020, e-pub. Apr. 30, 2020). "Biochemical Characterization of SARS-CoV-2 Nucleocapsid Protein," Biochem. Biophys. Res. Commun. 527(3):618-623.
Zhang, B.-Z. et al. (2020, e-pub. Jul. 1, 2020). "Mining of Epitopes On Spike Protein of SARS-CoV-2 From COVID-19 Patients," Cell Res. 30(8):702-704.
Zhang, J. et al. (2020). "Progress and Prospects on Vaccine Development Against SARS-CoV-2," Vaccines 8:153, 12 pages.
Zhao, K. et al. (2011, e-pub. Jul. 13, 2011). "The Immune Responses of HLA-A*0201 Restricted SARS-CoV S Peptide-Specific CD8+ T Cells are Augmented in Varying Degrees by CpGODN, PolyI:C and R848," Vaccine 29:6670-6678.
Zhou, P. et al. (2020, e-pub. Feb. 3, 2020). "A Pneumonia Outbreak Associated With a New Coronavirus of Probable Bat Origin," Nature, 579:270-273, 20 pages.
Zhu, N. et al. (2020, e-pub. Jan. 24, 2020). "A Novel Coronavirus From Patients With Pneumonia In China 2019," N Engl. J. Med. 382(8):727-733.
Weissman, D. et al. (Jan. 13, 2021). "D614G Spike Mutation Increase SARS CoV-2 Susceptibility to Neutralization," Cell Host of Microb. 29:23-31.

(56) References Cited

OTHER PUBLICATIONS

Xiong, X. et al. (Oct. 1, 2020). "A Thermostable, Closed SARS-CoV-2 Spike Protein Trimer," Nat. Struct. Mol. Biol. 27(10):934-941, 27 pages.
Kobinger, G.P. et al. (2007, e-pub. May 7, 2007). "Adenovirus-Based Vaccine Prevents Pneumonia In Ferrets Challenged With The SARS Coronavirus and Stimulates Robust Immune Responses In Macaques," Vaccine. 25(28):5220-5231.
Kulkarni, R. (Nov. 2019). "Antibody-Dependent Enhancement of Viral Infections," Dynamics of Immune Activation in Viral Diseases 5:9-41.
Kuo, T.-Y. et al. (2020). "Development of CpG-Adjuvanted Stable Prefusion SARS-CoV-2 Spike Antigen As a Subunit Vaccine Against COVID-19," Scientific Reports, 10:20085, 10 pages.
Lambert, P.-H. et al. (2020, e-pub. May 25, 2020). "Consensus Summary Report For CEPI/BC Mar. 12-13, 2020 Meeting: Assessment of Risk of Disease Enhancement With COVID-19 Vaccines," Vaccine 38(31):4783-4791, 10 pages.
Lan J. et al. (2014, e-pub. Nov. 18, 2014). "Tailoring Subunit Vaccine Immunity With Adjuvant Combinations and Delivery Routes Using the Middle East Respiratory Coronavirus (MERS-CoV) Receptor-Binding Domain As an Antigen," PLoS ONE 9(11):e112602, 9 pages.
Latimer, L.J.P. et al. (Oct. 1995). "Specificity of Monoclonal Antibodies Produced Against Phosphorothioate and Ribo Modified DNAs," Mol. Immunol. 32(14/15):1057-1064.
Lazarus, R. et al. (2022, e-pub. Sep. 5, 2022). "Immunogenicity and Safety of an Inactivated Whole-Virus COVID-19 Vaccine (VLA2001) Compared with the Adenoviral Vector Vaccine ChAdOx1-S in Adults in the UK (COVCOMPARE): Interim Analysis of a Randomised, Controlled, Phase 3, Immunobridging Trial," Lancet Infect. Dis. 22:1716-1727, 12 pages.
Letko, M. et al. (2020, e-pub. Feb. 24, 2020). "Functional Assessment of Cell Entry and Receptor Usage For SARS-CoV-2 and Other Lineage B Betacoronaviruses," Nature Microbiology, 5(4):562-569.
Li, J.-Y. et al. (2020, e-pub. Feb. 2020). "The Epidemic of 2019-Novel-Coronavirus (2019-nCoV) Pneumonia and Insights For Emerging Infectious Diseases In The Future," Microbes Infect. 22(2):80-85.
Liang, J.G. et al. (2021, e-pub. Mar. 1, 2021). "S-Trimer, a COVID-19 Subunit Vaccine Candidate, Induces Protective Immunity In Nonhuman Primates," Nat Commun. 12(1):1346, 12 pages.
Lien, C.-E. et al. (2021, e-pub Apr. 22, 2021). CpG-Adjuvanted Stable Prefusion SARS-CoV-2 Spike Protein Protected Hamsters From SARS-CoV-2 Challenge, Scientific Reports, 11: 8761. 7 pages.
Lin, J.-T. et al. (2007). "Safety and Immunogenicity From a Phase I Trial of Inactivated Severe Acute Respiratory Syndrome Corona Virus Vaccine," Antivir. Ther. 12(7):1107-1113.
Luo, F. et al. (2018, e-pub. Mar. 14, 2018). "Evaluation of Antibody-Dependent Enhancement of SARS-CoV Infection In Rhesus Macaques Immunized With an Inactivated SARS-CoV Vaccine," Virol Sin. 33(2):201-204.
Maisonnasse, P. et al. (2020, e-pub. Jul. 22, 2020). "Hydroxychloroquine Use Against SARS-CoV-2 Infection In Non-Human Primates," Nature 585(7826):584-587 and Supplemental Information, 18 pages.
Needleman, S. B. et al. (Mar. 1970). "A General Method Applicable to the Search for Similarities in the Amino Acid sequence of Two Proteins," J. Mol. Biol. 48:443-453.
Ng, M.-L. et al. (Dec. 2003). "Proliferative Growth of SARS Coronavirus In Vero E6 Cells," J. Gen. Virol. 84(12):3291-3303.
Ou, X. et al. (Mar. 27, 2020). "Characterization of Spike Glycoprotein of SARS-CoV-2 on Virus Entry and Its Immune Cross-Reactivity With SARS-CoV," Nat. Commun. 11(1):1620.
Pearson, W.R. et al. (Apr. 1988). "Improved Tools For Biological Sequence Comparison," Proc. Natl. Acad. Sci. USA 85(8):2444-2448.
Petrovsky, N. (Dec. 31, 2016). "SARS Coronavirus Infections of the Lower Respiratory Tract and Their Prevention," Chapter 3—The Microbiology of Respiratory System Infections, pp. 45-53.
Pramanick, S. et al. (Mar. 2013). "Excipient Selection In Parenteral Formulation Development," Pharma Times 45(3):65-77.
Rabaan, A.A. et al. (Apr. 7, 2020). "SARS-CoV-2/COVID-19 and Advances in Developing Potential Therapeutics and Vaccines To Counter This Emerging Pandemic," 19:40, 37 pages.
Ragan, I.K. et al. (2021, e-pub. Apr. 1, 2021). "A Whole Virion Vaccine for COVID-19 Produced via a Novel Inactivation Method and Preliminary Demonstration of Efficacy in an Animal Challenge Model," Vaccines, 9:340, 24 pages.
Rauch, S. et al. (2018, e-pub. Sep. 19, 2018). "New Vaccine Technologies To Combat Outbreak Situations," Front. Immunol. 9:1963, 38 pages.
Richmond, P. et al. (2021, e-pub. Jan. 29, 2021). "Safety and Immunogenicity of S-Trimer (SCB-2019), A Protein Subunit Vaccine Candidate For COVID-19 In Healthy Adults: A Phase 1, Randomised, Double-Blind, Placebo-Controlled Trial," Lancet 397:682-694.
Roberts, A. et al. (2008, e-pub. May 11, 2007). "Animal Models and Vaccines For SARS-CoV Infection," Virus Res. 133(1):20-32.
Roberts, A. et al. (May 2005). "Aged BALB/c Mice as a Model For Increased Severity Of Severe Acute Respiratory Syndrome In Elderly Humans," J. Virol. 79(9):5833-5838.
Sah, R. et al. (Mar. 12, 2020). "Complete Genome Sequence of a 2019 Novel Coronavirus (SARS-CoV-2) Strain Isolated In Nepal," Microbiol. Resour. Announc. 9(11):e00169-20, 3 pages.
Schlegl, R. et al. (2015, e-pub. Jun. 19, 2015). "Influence of Elemental Impurities In Aluminum Hydroxide Adjuvant on The Stability of Inactivated Japanese Encephalitis Vaccine, IXIARO®," Vaccine. 33(44):5989-5996.
See, R.H. et al. (Sep. 2008). "Severe Acute Respiratory Syndrome Vaccine Efficacy In Ferrets: Whole Killed Virus and Adenovirus-Vectored Vaccines," J Gen Virol. 89(Pt 9):2136-2146.
Sekimukai, H. et al. (2020, e-pub. Nov. 2019). "Gold Nanoparticle-Adjuvanted S Protein Induces a Strong Antigen-Specific IgG Response Against Severe Acute Respiratory Syndrome-Related Coronavirus Infection, But Fails To Induce Protective Antibodies and Limit Eosinophilic Infiltration In Lungs," Microbiol. Immunol. 64(1):33-51.
Shah, R.R. et al. (2017). "Chapter 1: Overview of Vaccine Adjuvants: Introduction, History, and current Status," Methods Mol. Biol. 1494:1-13.
Shang, J. et al. (2020, e-pub. Mar. 30, 2020). "Structural Basis of Receptor Recognition By SARS-CoV-2," Nature. 581(7807):221-224, 18 pages.
Shang, W. et al. (Mar. 6, 2020). "The Outbreak of SARS-CoV-2 Pneumonia Calls For Viral Vaccines," NPJ Vaccines 5(1):18, 3 pages.
Shanmugaraj, B. et al. (Feb. 22, 2020). "Emergence of Novel Coronavirus 2019-nCoV: Need For Rapid Vaccine and Biologics Development," Pathogens 9(2):148, 10 pages.
She, Y.-M. et al. (Dec. 2013). "Surface Modifications of Influenza Proteins Upon Virus Inactivation By β-propiolactone," Proteomics 13(23-24):3537-3547.
Shi, Y. et al. (2020, e-pub. Mar. 23, 2020). "COVID-19 Infection: The Perspectives On Immune Responses," Cell Death Differ. 27(5):1451-1454.
Spruth, M. et al. (2006, e-pub. Aug. 26, 2005). "A Double-Inactivated Whole Virus Candidate SARS Coronavirus Vaccine Stimulates Neutralising and Protective Antibody Responses," Vaccine 24(5):652-661.
Srivastava, A.K. et al. (Aug. 14, 2001). "A Purified Inactivated Japanese Encephalitis Virus Vaccine Made In Vero Cells," Vaccine 19(31):4557-4565.
Subbarao, K. et al. (Apr. 2004). "Prior Infection and Passive Transfer Of Neutralizing Antibody Prevent Replication of Severe Acute Respiratory Syndrome Corona Virus In The Respiratory Tract Of Mice," J. Virol. 78(7):3572-3577.
Szurgot, I. et al. (Feb. 4, 2021). "DNA-Launched RNA Replicon Vaccines Induce Potent Anti-SARS-CoV-2 Immune Responses In Mice," Sci. Rep. 11(1):3125, 13 pages.
Tetro, J.A. (2020, e-pub. Feb. 22, 2020). Is COVID-19 Receiving ADE From Other Coronaviruses? Microbes Infect. 22(2):72-73.

(56) References Cited

OTHER PUBLICATIONS

Thomas, L.J. et al. (2009, e-pub. Feb. 1, 2009). "Co-Administration of a CpG Adjuvant (VaxImmune, CPG 7909) With CETP vaccines Increased Immunogenicity In Rabbits and Mice," Hum Vaccin. 5(2):79-84.
Tian, X. et al. (2020, e-pub. Feb. 17, 2020). "Potent Binding of 2019 Novel Coronavirus Spike Protein By a SARS Coronavirus-Specific Human Monoclonal Antibody," Emerg. Microbes Infect. 9(1):382-385.
Tian, Y. et al. (Apr. 28, 2017). "The Novel Complex Combination of Alum, CpG ODN and HH2 As Adjuvant In Cancer Vaccine Effectively Suppresses Tumor Growth in vivo," Oncotarget. 8(28):45951-45964.
Tseng, C.-T. et al. (2012, e-pub. Apr. 20, 2012). "Immunization with SARS Coronavirus Vaccines Leads to Pulmonary Immunopathology on Challenge with the SARS Virus," PloS ONE, 7(4):e35421, 13 pages.
Tseng, C.-T.K. et al. (2007, e-pub. Nov. 15, 2006). "Severe Acute Respiratory Syndrome Coronavirus Infection of Mice Transgenic For The Human Angiotensin-Converting Enzyme 2 Virus Receptor," J Virol. 81(3):1162-1173.
Uittenbogaard, J.P. et al. (2011, e-pub. Aug. 25, 2011). "Reactions of Beta-Propiolactone With Nucleobase Analogues, Nucleosides, and Peptides: Implications For The Inactivation of Viruses," J. Biol. Chem. 286(42):36198-36214.
Walls, A. C. et al. (Apr. 16, 2020). "Structure, Function, and Antigenicity of the SARS-CoV-2 Spike Glycoprotein," Cell 180(2):281-292, 38 pages.
Wan, Y. et al. (2020, e-pub. Feb. 14, 2020). "Molecular Mechanism For Antibody-Dependent Enhancement of Coronavirus Entry," J. Virol. 94(5):e02015-19, 15 pages.
Wang, B. et al. (2020). "The Potential for Antibody-Dependent Enhancement of SARS-CoV-2 Infection: Transnational Implications for Vaccine Development," Journal of Clinical and Translational Science 5:e2, 4 pages.
Jie Li, Immunogenicity and Protection Efficacy of Monomeric and Trimeric Recombinant SARS Coronavirus Spike Protein Subunit Vaccine Candidates, Viral Immunology, Apr. 2013, pp. 126-132, v.26, No. 2, Mary Ann Liebert, Inc., Larchmont, NY, USA.
Jesper Pallesen, Immunogenicity and structures of a rationally designed prefusion MERS-CoV spike antigen, PNAS, Aug. 14, 2017, pp. E7348-E7357, v.114, No. 35, National Academy of Sciences, Washington, D.C., USA.
Shuting Shi, Vaccine adjuvants: Understanding the structure and mechanism of adjuvanticity, Vaccine, May 27, 2019, pp. 3167-3178, v.37, issue 24, Elsevier, Amsterdam, Netherlands.
Daniel Wrapp, Supplementary Materials for Cryo-EM structure of the 2019-nCoV spike in the prefusion conformation, Science, Feb. 19, 2020, pp. 1260-1263, v.367, No. 6483, American Association for the Advancement of Science, Washington, D.C., USA.

\* cited by examiner

SEQUENCE LISTING

```
<160> NUMBER OF SEQ ID NOS: 17

<210> SEQ ID NO 1
<211> LENGTH: 1195
<212> TYPE: PRT
<213> ORGANISM: Artificial Sequence
<220> FEATURE:
<223> OTHER INFORMATION: Recombinant coronavirus spike protein
```

```
<400> SEQUENCE: 1

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415
```

-continued

```
Thr Gly Cys Val Ile Ala Trp Asn Ser Asn Leu Asp Ser Lys Val
            420                 425                 430
Gly Gly Asn Tyr Asn Tyr Leu Tyr Arg Leu Phe Arg Lys Ser Asn Leu
            435                 440                 445
Lys Pro Phe Glu Arg Asp Ile Ser Thr Glu Ile Tyr Gln Ala Gly Ser
    450                 455                 460
Thr Pro Cys Asn Gly Val Glu Gly Phe Asn Cys Tyr Phe Pro Leu Gln
465                 470                 475                 480
Ser Tyr Gly Phe Gln Pro Thr Asn Gly Val Gly Tyr Gln Pro Tyr Arg
                485                 490                 495
Val Val Val Leu Ser Phe Glu Leu Leu His Ala Pro Ala Thr Val Cys
            500                 505                 510
Gly Pro Lys Lys Ser Thr Asn Leu Val Lys Asn Lys Cys Val Asn Phe
            515                 520                 525
Asn Phe Asn Gly Leu Thr Gly Thr Gly Val Leu Thr Glu Ser Asn Lys
            530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
            580                 585                 590
Asn Gln Val Ala Val Leu Tyr Gln Asp Val Asn Cys Thr Glu Val Pro
            595                 600                 605
Val Ala Ile His Ala Asp Gln Leu Thr Pro Thr Trp Arg Val Tyr Ser
            610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Gly Ser Ala Ser
            660                 665                 670
Ser Val Ala Ser Gln Ser Ile Ile Ala Tyr Thr Met Ser Leu Gly Ala
            675                 680                 685
Glu Asn Ser Val Ala Tyr Ser Asn Asn Ser Ile Ala Ile Pro Thr Asn
    690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
            740                 745                 750
Ala Leu Thr Gly Ile Ala Val Glu Gln Asp Lys Asn Thr Gln Glu Val
            755                 760                 765
Phe Ala Gln Val Lys Gln Ile Tyr Lys Thr Pro Pro Ile Lys Asp Phe
            770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
            820                 825                 830
```

```
Ala Arg Asp Leu Ile Cys Ala Gln Lys Phe Asn Gly Leu Thr Val Leu
    835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln
    1010                1015                1020

Ser Lys Arg Val Asp Phe Cys Gly Lys Gly Tyr His Leu Met Ser
    1025                1030                1035

Phe Pro Gln Ser Ala Pro His Gly Val Val Phe Leu His Val Thr
    1040                1045                1050

Tyr Val Pro Ala Gln Glu Lys Asn Phe Thr Thr Ala Pro Ala Ile
    1055                1060                1065

Cys His Asp Gly Lys Ala His Phe Pro Arg Glu Gly Val Phe Val
    1070                1075                1080

Ser Asn Gly Thr His Trp Phe Val Thr Gln Arg Asn Phe Tyr Glu
    1085                1090                1095

Pro Gln Ile Ile Thr Thr Asp Asn Thr Phe Val Ser Gly Asn Cys
    1100                1105                1110

Asp Val Val Ile Gly Ile Val Asn Asn Thr Val Tyr Asp Pro Leu
    1115                1120                1125

Gln Pro Glu Leu Asp Ser Phe Lys Glu Glu Leu Asp Lys Tyr Phe
    1130                1135                1140

Lys Asn His Thr Ser Pro Asp Val Asp Leu Gly Asp Ile Ser Gly
    1145                1150                1155

Ile Asn Ala Ser Val Val Asn Ile Gln Lys Glu Ile Asp Arg Leu
    1160                1165                1170

Asn Glu Val Ala Lys Asn Leu Asn Glu Ser Leu Ile Asp Leu Gln
    1175                1180                1185

Glu Leu Gly Lys Tyr Glu Gln
    1190                1195

<210> SEQ ID NO 2
<211> LENGTH: 32
<212> TYPE: PRT
<213> ORGANISM: Artificial Sequence
<220> FEATURE:
<223> OTHER INFORMATION: T4 fibritin trimerization domain
```

<400> SEQUENCE: 2

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu Gly Arg Ser
            20                  25                  30

<210> SEQ ID NO 3
<211> LENGTH: 9
<212> TYPE: PRT
<213> ORGANISM: Artificial Sequence
<220> FEATURE:
<223> OTHER INFORMATION: HRV3C protease cleavage site

<400> SEQUENCE: 3

Leu Glu Val Leu Phe Gln Gly Pro Gly
1               5

<210> SEQ ID NO 4
<211> LENGTH: 31
<212> TYPE: PRT
<213> ORGANISM: Artificial Sequence
<220> FEATURE:
<223> OTHER INFORMATION: Twin-Strep Tag

<400> SEQUENCE: 4

Ser Ala Trp Ser His Pro Gln Phe Glu Lys Gly Gly Gly Ser Gly Gly
1               5                   10                  15

Gly Gly Ser Gly Gly Ser Ala Trp Ser His Pro Gln Phe Glu Lys
            20                  25                  30

<210> SEQ ID NO 5
<211> LENGTH: 1227
<212> TYPE: PRT
<213> ORGANISM: Artificial Sequence
<220> FEATURE:
<223> OTHER INFORMATION: Recombinant coronavirus spike protein

<400> SEQUENCE: 5

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu

```
                        165                 170                 175
Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
        210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590
```

```
Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Gly Ser Ala Ser
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
            850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
            930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
                980                 985                 990

Thr Tyr Val Thr Gln Gln Leu Ile  Arg Ala Ala Glu Ile  Arg Ala Ser
            995                 1000                1005
```

```
Ala Asn Leu Ala Ala Thr Lys Met Ser Glu Cys Val Leu Gly Gln
    1010                1015                1020

Ser Lys Arg Val Asp Phe Cys Gly Lys Gly Tyr His Leu Met Ser
    1025                1030                1035

Phe Pro Gln Ser Ala Pro His Gly Val Val Phe Leu His Val Thr
    1040                1045                1050

Tyr Val Pro Ala Gln Glu Lys Asn Phe Thr Thr Ala Pro Ala Ile
    1055                1060                1065

Cys His Asp Gly Lys Ala His Phe Pro Arg Glu Gly Val Phe Val
    1070                1075                1080

Ser Asn Gly Thr His Trp Phe Val Thr Gln Arg Asn Phe Tyr Glu
    1085                1090                1095

Pro Gln Ile Ile Thr Thr Asp Asn Thr Phe Val Ser Gly Asn Cys
    1100                1105                1110

Asp Val Val Ile Gly Ile Val Asn Asn Thr Val Tyr Asp Pro Leu
    1115                1120                1125

Gln Pro Glu Leu Asp Ser Phe Lys Glu Glu Leu Asp Lys Tyr Phe
    1130                1135                1140

Lys Asn His Thr Ser Pro Asp Val Asp Leu Gly Asp Ile Ser Gly
    1145                1150                1155

Ile Asn Ala Ser Val Val Asn Ile Gln Lys Glu Ile Asp Arg Leu
    1160                1165                1170

Asn Glu Val Ala Lys Asn Leu Asn Glu Ser Leu Ile Asp Leu Gln
    1175                1180                1185

Glu Leu Gly Lys Tyr Glu Gln Gly Ser Gly Tyr Ile Pro Glu Ala
    1190                1195                1200

Pro Arg Asp Gly Gln Ala Tyr Val Arg Lys Asp Gly Glu Trp Val
    1205                1210                1215

Leu Leu Ser Thr Phe Leu Gly Arg Ser
    1220                1225

<210> SEQ ID NO 6
<211> LENGTH: 1233
<212> TYPE: PRT
<213> ORGANISM: Artificial Sequence
<220> FEATURE:
<223> OTHER INFORMATION: Recombinant coronavirus spike protein

<400> SEQUENCE: 6

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                    85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
            115                 120                 125
```

-continued

```
Gly Val Tyr Tyr His Lys Asn Asn Lys Ser Trp Met Glu Ser Glu Phe
130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
```

```
                545                 550                 555                 560
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
                580                 585                 590
Asn Gln Val Ala Val Leu Tyr Gln Asp Val Asn Cys Thr Glu Val Pro
                595                 600                 605
Val Ala Ile His Ala Asp Gln Leu Thr Pro Thr Trp Arg Val Tyr Ser
                610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Gly Ser Ala Ser
                660                 665                 670
Ser Val Ala Ser Gln Ser Ile Ile Ala Tyr Thr Met Ser Leu Gly Ala
                675                 680                 685
Glu Asn Ser Val Ala Tyr Ser Asn Asn Ser Ile Ala Ile Pro Thr Asn
                690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
                740                 745                 750
Ala Leu Thr Gly Ile Ala Val Glu Gln Asp Lys Asn Thr Gln Glu Val
                755                 760                 765
Phe Ala Gln Val Lys Gln Ile Tyr Lys Thr Pro Pro Ile Lys Asp Phe
                770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
                820                 825                 830
Ala Arg Asp Leu Ile Cys Ala Gln Lys Phe Asn Gly Leu Thr Val Leu
                835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
                900                 905                 910
Gln Phe Asn Ser Ala Ile Gly Lys Ile Gln Asp Ser Leu Ser Ser Thr
                915                 920                 925
Ala Ser Ala Leu Gly Lys Leu Gln Asp Val Val Asn Gln Asn Ala Gln
                930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Pro Pro Glu Ala
                965                 970                 975
```

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn Leu Ala Ala Thr Lys  Met Ser Glu Cys Val  Leu Gly Gln
    1010                1015                1020

Ser Lys Arg Val Asp Phe Cys  Gly Lys Gly Tyr His  Leu Met Ser
    1025                1030                1035

Phe Pro Gln Ser Ala Pro His  Gly Val Val Phe Leu  His Val Thr
    1040                1045                1050

Tyr Val Pro Ala Gln Glu Lys  Asn Phe Thr Ala  Pro Ala Ile
    1055                1060                1065

Cys His Asp Gly Lys Ala His  Phe Pro Arg Glu Gly  Val Phe Val
    1070                1075                1080

Ser Asn Gly Thr His Trp Phe  Val Thr Gln Arg Asn  Phe Tyr Glu
    1085                1090                1095

Pro Gln Ile Ile Thr Thr Asp  Asn Thr Phe Val Ser  Gly Asn Cys
    1100                1105                1110

Asp Val Val Ile Gly Ile Val  Asn Asn Thr Val Tyr  Asp Pro Leu
    1115                1120                1125

Gln Pro Glu Leu Asp Ser Phe  Lys Glu Glu Leu Asp  Lys Tyr Phe
    1130                1135                1140

Lys Asn His Thr Ser Pro Asp  Val Asp Leu Gly Asp  Ile Ser Gly
    1145                1150                1155

Ile Asn Ala Ser Val Val Asn  Ile Gln Lys Glu Ile  Asp Arg Leu
    1160                1165                1170

Asn Glu Val Ala Lys Asn Leu  Asn Glu Ser Leu Ile  Asp Leu Gln
    1175                1180                1185

Glu Leu Gly Lys Tyr Glu Gln  Gly Ser Gly Tyr Ile  Pro Glu Ala
    1190                1195                1200

Pro Arg Asp Gly Gln Ala Tyr  Val Arg Lys Asp Gly  Glu Trp Val
    1205                1210                1215

Leu Leu Ser Thr Phe Leu Gly  Arg Ser Leu Glu Val  Leu Phe Gln
    1220                1225                1230

<210> SEQ ID NO 7
<211> LENGTH: 1273
<212> TYPE: PRT
<213> ORGANISM: Severe Acute Respiratory Syndrome Coronavirus 2

<400> SEQUENCE: 7

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser

```
            100             105             110
Lys Thr Gln Ser Leu Leu Ile Val Asn Asn Ala Thr Asn Val Val Ile
        115             120             125
Lys Val Cys Glu Phe Gln Phe Cys Asn Asp Pro Phe Leu Gly Val Tyr
    130             135             140
Tyr His Lys Asn Asn Lys Ser Trp Met Glu Ser Glu Phe Arg Val Tyr
145             150             155             160
Ser Ser Ala Asn Asn Cys Thr Phe Glu Tyr Val Ser Gln Pro Phe Leu
            165             170             175
Met Asp Leu Glu Gly Lys Gln Gly Asn Phe Lys Asn Leu Arg Glu Phe
        180             185             190
Val Phe Lys Asn Ile Asp Gly Tyr Phe Lys Ile Tyr Ser Lys His Thr
    195             200             205
Pro Ile Asn Leu Val Arg Asp Leu Pro Gln Gly Phe Ser Ala Leu Glu
210             215             220
Pro Leu Val Asp Leu Pro Ile Gly Ile Asn Ile Thr Arg Phe Gln Thr
225             230             235             240
Leu Leu Ala Leu His Arg Ser Tyr Leu Thr Pro Gly Asp Ser Ser Ser
            245             250             255
Gly Trp Thr Ala Gly Ala Ala Ala Tyr Tyr Val Gly Tyr Leu Gln Pro
        260             265             270
Arg Thr Phe Leu Leu Lys Tyr Asn Glu Asn Gly Thr Ile Thr Asp Ala
    275             280             285
Val Asp Cys Ala Leu Asp Pro Leu Ser Glu Thr Lys Cys Thr Leu Lys
290             295             300
Ser Phe Thr Val Glu Lys Gly Ile Tyr Gln Thr Ser Asn Phe Arg Val
305             310             315             320
Gln Pro Thr Glu Ser Ile Val Arg Phe Pro Asn Ile Thr Asn Leu Cys
            325             330             335
Pro Phe Gly Glu Val Phe Asn Ala Thr Arg Phe Ala Ser Val Tyr Ala
        340             345             350
Trp Asn Arg Lys Arg Ile Ser Asn Cys Val Ala Asp Tyr Ser Val Leu
    355             360             365
Tyr Asn Ser Ala Ser Phe Ser Thr Phe Lys Cys Tyr Gly Val Ser Pro
370             375             380
Thr Lys Leu Asn Asp Leu Cys Phe Thr Asn Val Tyr Ala Asp Ser Phe
385             390             395             400
Val Ile Arg Gly Asp Glu Val Arg Gln Ile Ala Pro Gly Gln Thr Gly
            405             410             415
Lys Ile Ala Asp Tyr Asn Tyr Lys Leu Pro Asp Asp Phe Thr Gly Cys
        420             425             430
Val Ile Ala Trp Asn Ser Asn Asn Leu Asp Ser Lys Val Gly Gly Asn
    435             440             445
Tyr Asn Tyr Leu Tyr Arg Leu Phe Arg Lys Ser Asn Leu Lys Pro Phe
450             455             460
Glu Arg Asp Ile Ser Thr Glu Ile Tyr Gln Ala Gly Ser Thr Pro Cys
465             470             475             480
Asn Gly Val Glu Gly Phe Asn Cys Tyr Phe Pro Leu Gln Ser Tyr Gly
            485             490             495
Phe Gln Pro Thr Asn Gly Val Gly Tyr Gln Pro Tyr Arg Val Val Val
        500             505             510
Leu Ser Phe Glu Leu Leu His Ala Pro Ala Thr Val Cys Gly Pro Lys
    515             520             525
```

```
Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
930                 935                 940
```

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 8
<211> LENGTH: 22
<212> TYPE: DNA
<213> ORGANISM: Artificial Sequence
<220> FEATURE:
<223> OTHER INFORMATION: CpG motif

<400> SEQUENCE: 8
tgactgtgaa cgttcgagat ga                                            22

```
<210> SEQ ID NO 9
<211> LENGTH: 24
<212> TYPE: DNA
<213> ORGANISM: Artificial Sequence
<220> FEATURE:
<223> OTHER INFORMATION: CpG motif

<400> SEQUENCE: 9
tcgtcgtttt gtcgttttgt cgtt                                          24

<210> SEQ ID NO 10
<211> LENGTH: 20
<212> TYPE: DNA
<213> ORGANISM: Artificial Sequence
<220> FEATURE:
<223> OTHER INFORMATION: CpG motif

<400> SEQUENCE: 10
ggtgcatcga tgcagggggg                                               20

<210> SEQ ID NO 11
<211> LENGTH: 22
<212> TYPE: DNA
<213> ORGANISM: Artificial Sequence
<220> FEATURE:
<223> OTHER INFORMATION: CpG motif

<400> SEQUENCE: 11
tccatggacg ttcctgagcg tt                                            22

<210> SEQ ID NO 12
<211> LENGTH: 22
<212> TYPE: DNA
<213> ORGANISM: Artificial Sequence
<220> FEATURE:
<223> OTHER INFORMATION: CpG motif

<400> SEQUENCE: 12
tcgtcgttcg aacgacgttg at                                            22

<210> SEQ ID NO 13
<211> LENGTH: 23
<212> TYPE: DNA
<213> ORGANISM: Artificial Sequence
<220> FEATURE:
<223> OTHER INFORMATION: CpG motif

<400> SEQUENCE: 13
tcgtcgacga tcggcgcgcg ccg                                           23

<210> SEQ ID NO 14
<211> LENGTH: 1208
<212> TYPE: PRT
<213> ORGANISM: Artificial Sequence
<220> FEATURE:
<223> OTHER INFORMATION: Recombinant coronavirus spike protein

<400> SEQUENCE: 14

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
```

```
                50                  55                  60
    Phe His Ala Ile His Val Ser Gly Thr Asn Gly Thr Lys Arg Phe Asp
    65                  70                  75                  80

Asn Pro Val Leu Pro Phe Asn Asp Gly Val Tyr Phe Ala Ser Thr Glu
                        85                  90                  95

Lys Ser Asn Ile Ile Arg Gly Trp Ile Phe Gly Thr Thr Leu Asp Ser
                    100                 105                 110

Lys Thr Gln Ser Leu Leu Ile Val Asn Asn Ala Thr Asn Val Val Ile
                115                 120                 125

Lys Val Cys Glu Phe Gln Phe Cys Asn Asp Pro Phe Leu Gly Val Tyr
                130                 135                 140

Tyr His Lys Asn Asn Lys Ser Trp Met Glu Ser Glu Phe Arg Val Tyr
    145                 150                 155                 160

Ser Ser Ala Asn Asn Cys Thr Phe Glu Tyr Val Ser Gln Pro Phe Leu
                    165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
                195                 200                 205

Pro Ile Asn Leu Val Arg Asp Leu Pro Gln Gly Phe Ser Ala Leu Glu
            210                 215                 220

Pro Leu Val Asp Leu Pro Ile Gly Ile Asn Ile Thr Arg Phe Gln Thr
    225                 230                 235                 240

Leu Leu Ala Leu His Arg Ser Tyr Leu Thr Pro Gly Asp Ser Ser Ser
                    245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
                275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
    305                 310                 315                 320

Gln Pro Thr Glu Ser Ile Val Arg Phe Pro Asn Ile Thr Asn Leu Cys
                    325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
    385                 390                 395                 400

Val Ile Arg Gly Asp Glu Val Arg Gln Ile Ala Pro Gly Gln Thr Gly
                    405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
    465                 470                 475                 480
```

```
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
        580                 585                 590

Gly Gly Val Ser Val Ile Thr Pro Gly Thr Asn Thr Ser Asn Gln Val
    595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895
```

```
Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln
    1205

<210> SEQ ID NO 15
<211> LENGTH: 26
<212> TYPE: DNA
<213> ORGANISM: Artificial Sequence
<220> FEATURE:
<223> OTHER INFORMATION: Forward primer

<400> SEQUENCE: 15
acaggtacgt taatagttaa tagcgt                                      26

<210> SEQ ID NO 16
<211> LENGTH: 22
<212> TYPE: DNA
```

```
<213> ORGANISM: Artificial Sequence
<220> FEATURE:
<223> OTHER INFORMATION: Reverse primer

<400> SEQUENCE: 16
atattgcagc agtacgcaca ca                                              22

<210> SEQ ID NO 17
<211> LENGTH: 26
<212> TYPE: DNA
<213> ORGANISM: Artificial Sequence
<220> FEATURE:
<223> OTHER INFORMATION: Probe

<400> SEQUENCE: 17
acactagcca tccttactgc gcttcg                                          26
```

IMMUNOGENIC COMPOSITION AGAINST SEVERE ACUTE RESPIRATORY SYNDROME CORONAVIRUS 2 (SARS-CoV-2)

CROSS-REFERENCE TO RELATED APPLICATIONS

This application claims priority to and the benefit of U.S. Provisional Application No. 63/040,696, filed on Jun. 18, 2020. This application is also a continuation application of International Application No. PCT/US21/20277, filed on Mar. 1, 2021, which itself claims priority to and the benefit of U.S. Provisional Application No. 62/983,737, filed on Mar. 1, 2020. The disclosure of each of the above applications is incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: P21-0142 Sequence Listing_ST25.txt, date recorded: Jun. 17, 2021, size: 56 KB). An identical copy of the Sequence Listing is attached following the specification.

BACKGROUND OF THE INVENTION

1. Field of the Invention

The present invention relates to an immunogenic composition against severe acute respiratory syndrome coronavirus 2 (SARS-CoV-2), especially to an immunogenic composition having a recombinant SARS-CoV-2 S protein and adjuvant.

2. Description of the Prior Art

On 31 Dec. 2019, the World Health Organization (WHO) was alerted to several cases of pneumonia in Wuhan City, Hubei Province of China. The viral pathogen did not match any other known virus and was later officially named "severe acute respiratory syndrome coronavirus 2 (SARS-CoV-2)." The official name of the disease caused by SARS-CoV-2 is coronavirus disease 2019 (COVID-19). Common symptoms of COVID-19 include fever, dry cough, fatigue, tiredness, muscle or body aches, sore throat, diarrhea, conjunctivitis, headache, loss of taste or smell, a rash on skin, and shortness of breath. While the majority of cases result in mild symptoms, some progress to acute respiratory distress syndrome (ARDS), precipitated by cytokine storm, multi-organ failure, septic shock, and blood clots. The first confirmed death from the coronavirus infection occurred on January 9, and as of 13 Jun. 2021, 175,306,598 confirmed cases of COVID-19, including 3,792,777 deaths, have been reported to the WHO. The numbers are still growing fast. 4

To reduce the risk of SARS-CoV-2 infection without curtailing everyday activities, a COVID-19 vaccine is needed. In particular, a COVID-19 vaccine that is able to rapidly induce an immune response against SARS-CoV-2 is urgently needed.

SUMMARY OF THE INVENTION

In one aspect, the present invention provides an immunogenic composition against a severe acute respiratory syndrome coronavirus 2 (SARS-CoV-2), comprising an antigenic recombinant protein and an adjuvant selected from the group consisting of an aluminum-containing adjuvant, an unmethylated cytosine-phosphate-guanosine (CpG) motif, and a combination thereof, wherein the antigenic recombinant protein substantially consists of residues 14-1208 of SARS-CoV-2 S protein with proline substitutions at residues 986 and 987 and a "GSAS" substitution at residues 682-685 and a C-terminal T4 fibritin trimerization domain.

In another aspect, the present invention provides a method for eliciting an immune response against a severe acute respiratory syndrome coronavirus 2 (SARS-CoV-2) in a subject in need thereof, comprising administering to the subject an effective amount of an immunogenic composition of the present invention.

In another aspect, the present invention provides a method for protecting a subject in need thereof from infection with severe acute respiratory syndrome coronavirus 2 (SARS-CoV-2), comprising administering to the subject an effective amount of the immunogenic composition of the present invention.

In another aspect, the present invention provides a method for preventing a subject in need thereof from contracting COVID-19 disease, comprising administering to the subject an effective amount of the immunogenic composition of the present invention.

These and other aspects will become apparent from the following description of the preferred embodiment taken in conjunction with the following drawings.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

and subjected to a neutralization assay with wild-type SARS-CoV-2 to determine neutralization antibody titers. p<0.01, *p<0.001.

Figure 5:
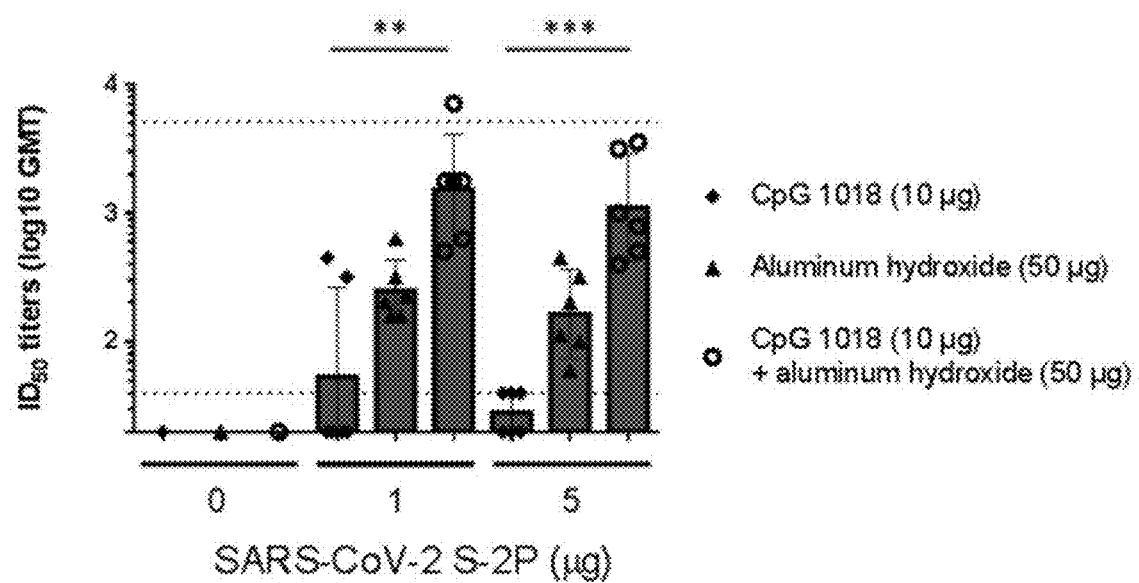
FIG. 5 shows neutralization of wild-type SARS-CoV-2 virus by antibodies induced by SARS-CoV-2 S-2P adjuvanted with CpG 1018 and aluminum hydroxide. The antisera were collected as described in FIG. 4 (N=6 per group)
Figure 6:
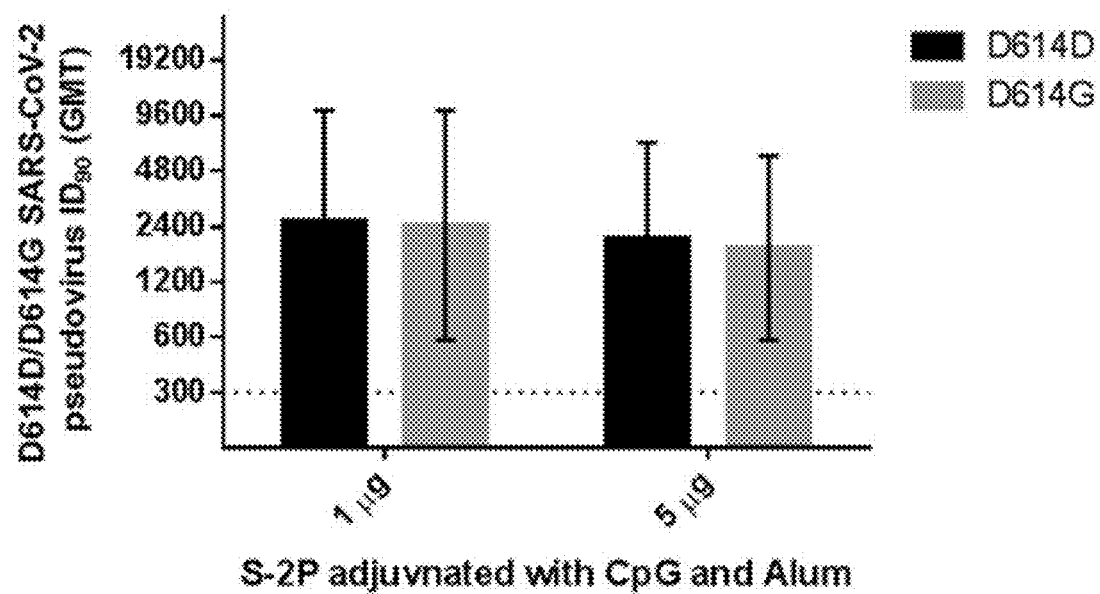

FIG. 6 shows inhibition of pseudoviruses carrying D614D (wild-type) or D614G (variant) versions of the spike protein by mice immunized with S-2P with CpG 1018 and aluminum hydroxide. The antisera of BALB/c mice immunized with 1 or 5 μg of S-2P with 10 μg CpG 1018 and 50 μg aluminum hydroxide as in FIG. 5 (N=5 per group due to assay capacity) were collected. Neutralization assays were performed with pseudoviruses with either D616D or D614G spike proteins.

Figure 7:
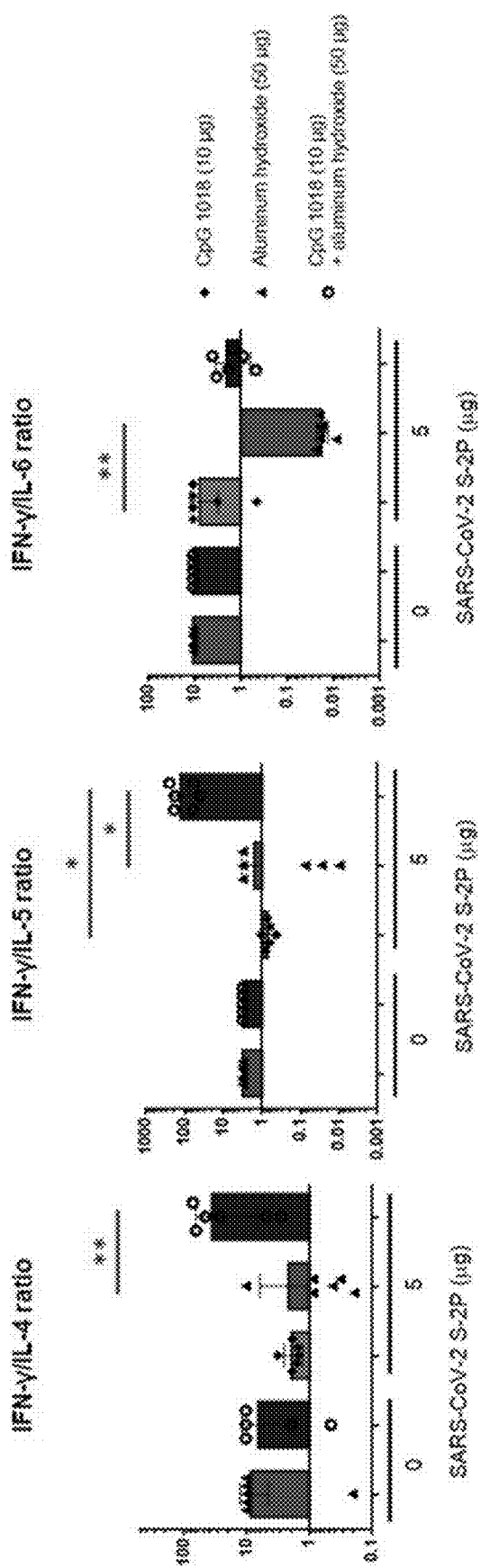

FIG. 7 shows IFN-γ/IL-4, IFN-γ/IL-5, and IFN-γ/IL-6 ratios. IFN-γ, IL-4, IL-5, and IL-6 values from the cytokine assays (N=6 per group) were used to calculate ratios. Ratio values greater than 1 indicate Th1 bias whereas ratio less than 1 indicate Th2 bias responses. *p<0.05, **p<0.01.

Figure 8B:
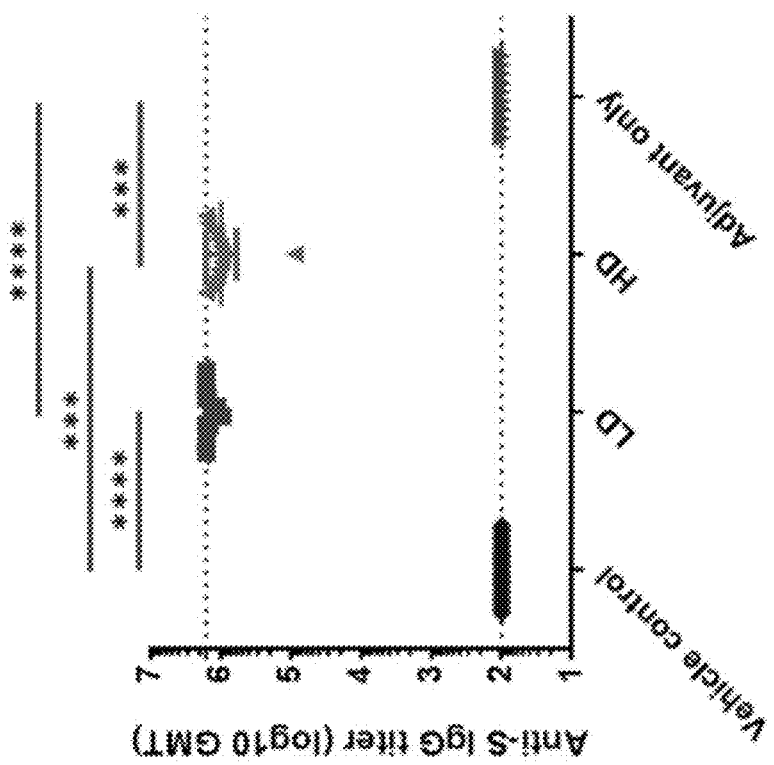
Figure 8A:
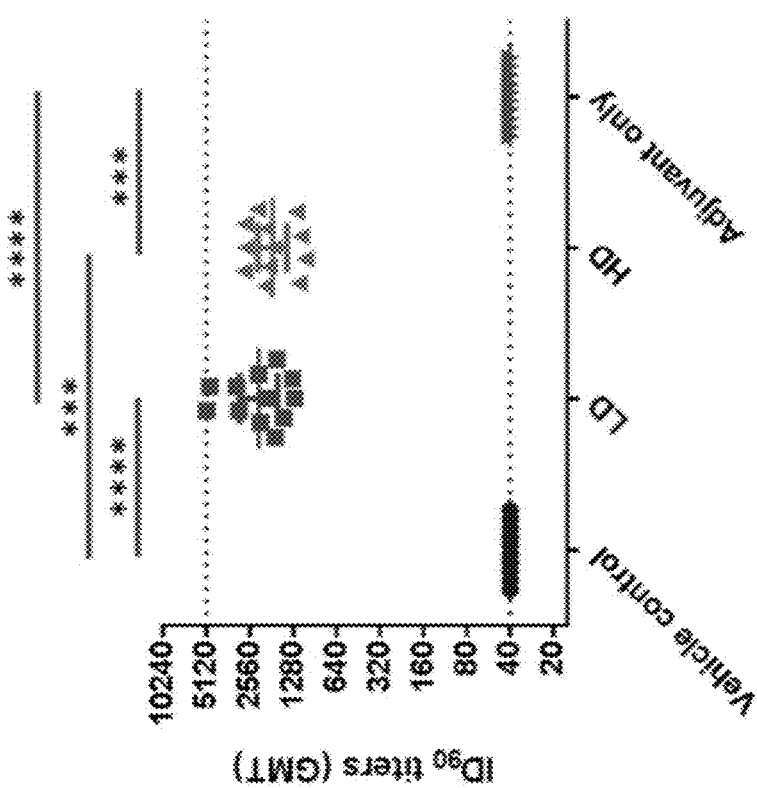

FIGS. 8A-8B show neutralizing antibody titers with pseudovirus assay in hamsters 2 weeks after second immunization. Hamsters (N=10 per group) were immunized twice at 3 weeks apart with vehicle control (PBS), 1 μg (LD) or 5 μg (HD) of S-2P adjuvanted with 150 μg CpG 1018 and 75 μg aluminum hydroxide, or with adjuvant alone. The antisera were harvested at 2 weeks after the second injection and subjected to neutralization assay with pseudovirus expressing SARS-CoV-2 spike protein to determine the $ID_{90}$ titers of neutralization antibodies (FIG. 8A) and total anti-S IgG antibody titers with ELISA (FIG. 8B). Results are presented as geometric mean with error bars representing 95% confidence interval and statistical significance calculated with Kruskal-Wallis with corrected Dunn's multiple comparisons test. Dotted lines represent lower and upper limits of detection (40 and 5120 in $ID_{90}$, 100 and 1,638,400 in IgG ELISA). *p<0.001, **p<0.0001.

Figure 9B:
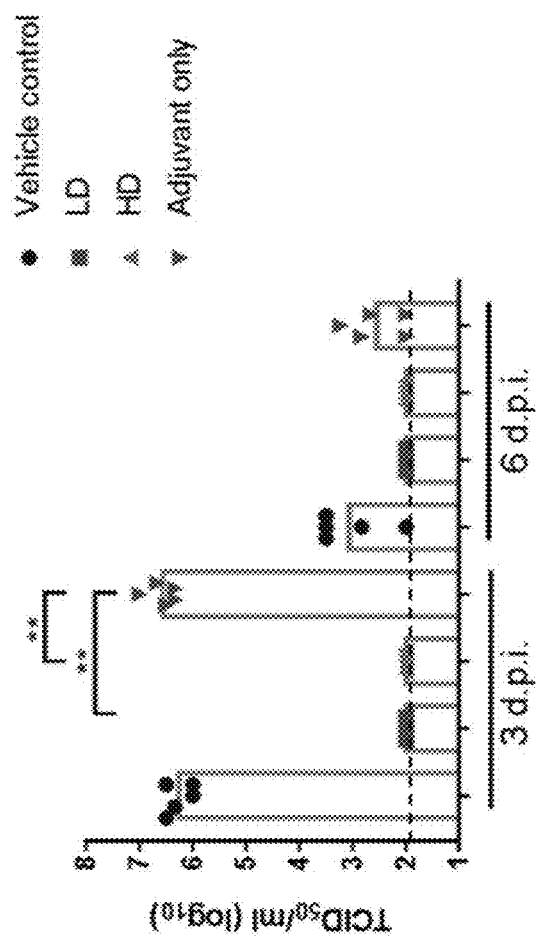
Figure 9A:
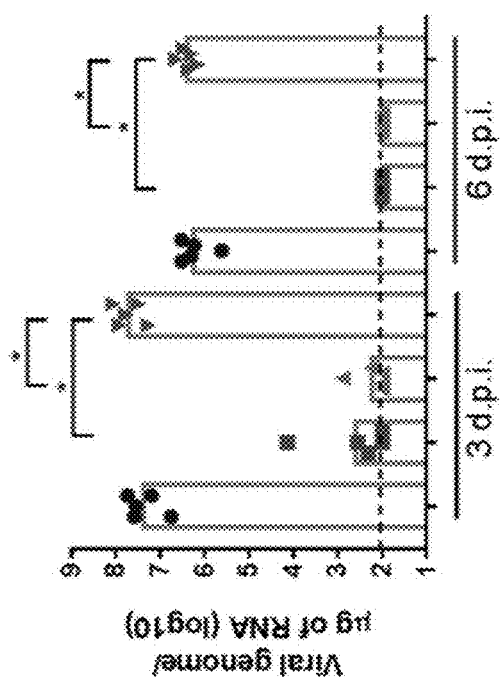

FIGS. 9A-9B show viral load in hamsters 3 or 6 days post infection (dpi) with SARS-CoV-2. The hamsters were euthanized at 3 or 6 dpi and lung tissue samples were collected for viral load determination by quantitative PCR of viral genome RNA (FIG. 9A), and $TCID_{50}$ assay for virus titer (FIG. 9B). Results are presented as geometric mean with error bars representing 95% confidence interval and statistical significance calculated with Kruskal-Wallis with corrected Dunn's multiple comparisons test. Dotted lines represent lower and limit of detection (100). *p<0.05, **p<0.01.

Figure 10:
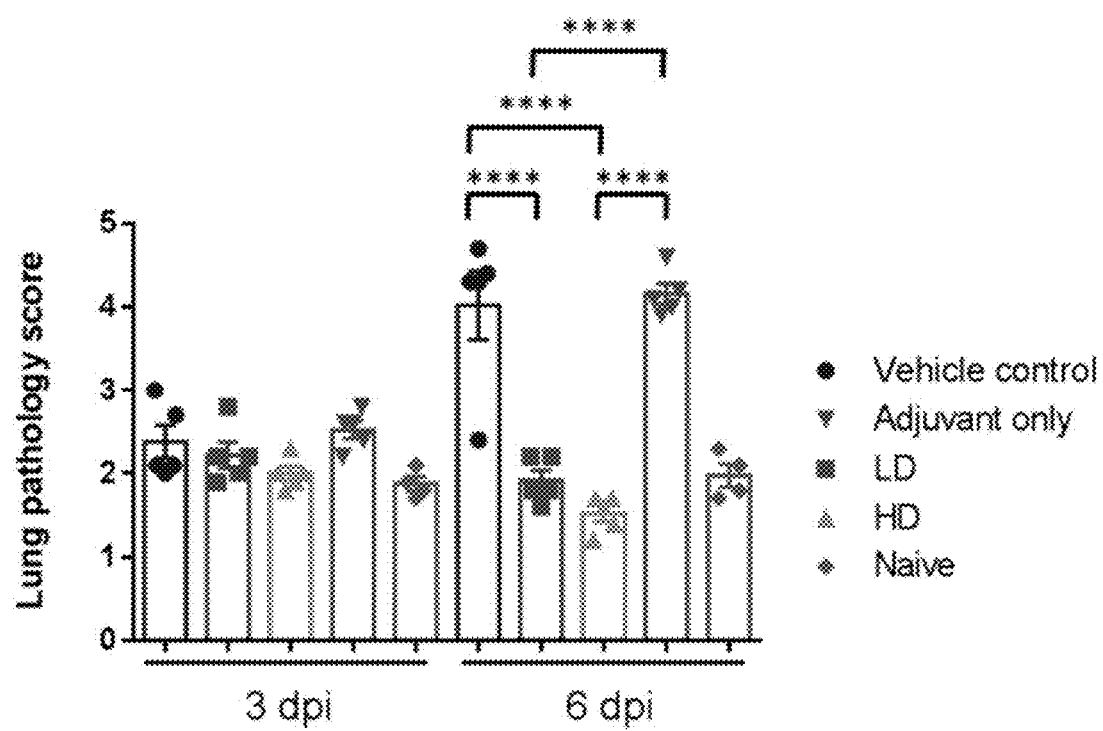

FIG. 10 shows lung pathology scoring in hamsters 3 or 6 days post infection (dpi) with SARS-CoV-2. The hamsters were euthanized at 3 or 6 dpi and lung tissue samples were collected for sectioning and staining. The histopathology sections were scored as outlined in the methods and the results tabulated. Results are presented as mean of lung pathology scores with error bars representing standard error and statistical significance calculated with one-way ANOVA with Tukey's multiple comparisons test. ****p<0.0001.

Figure 11:
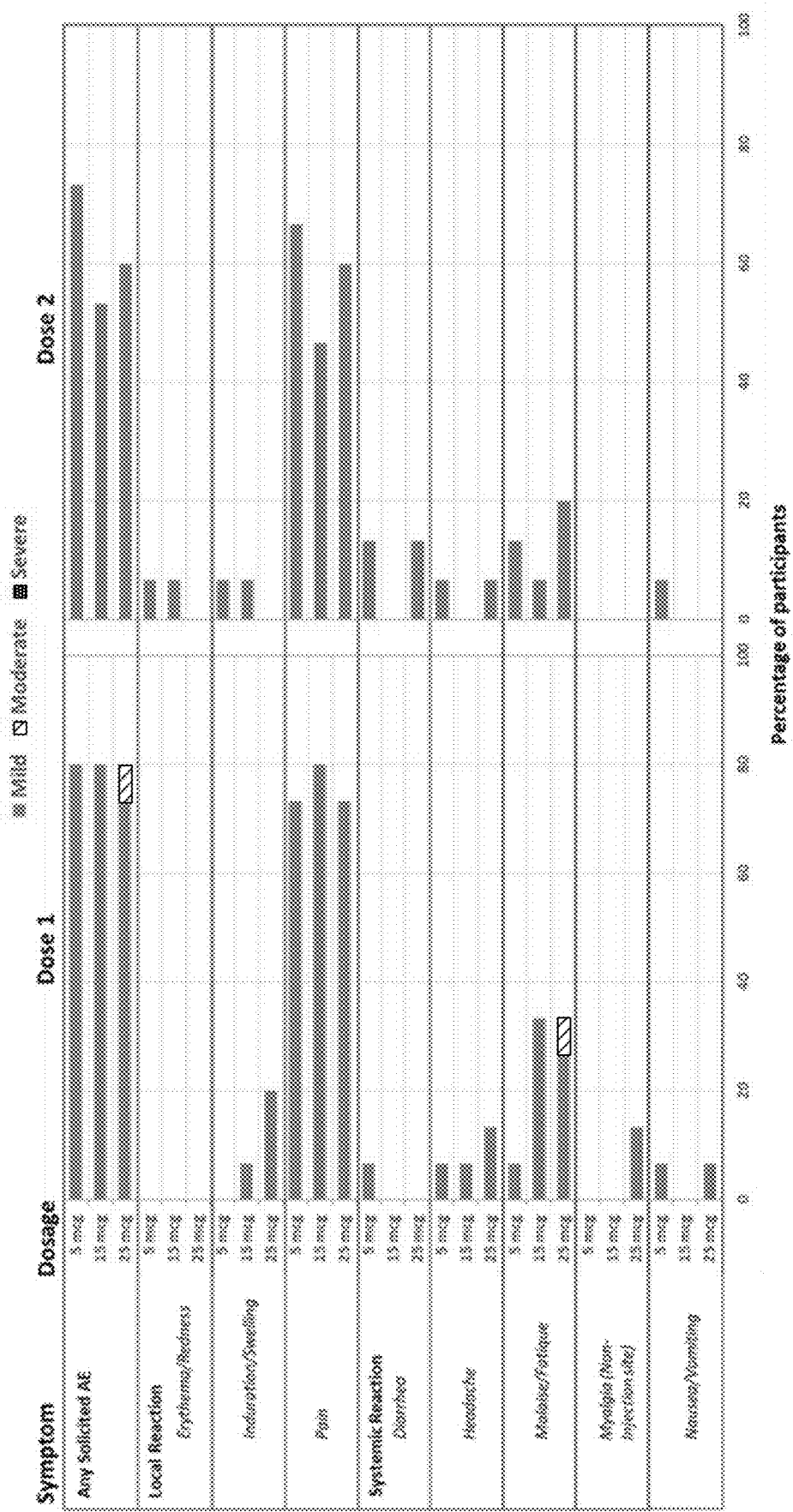

FIG. 11 shows summary of solicited adverse events in a Phase I clinical trial. Participants were asked to record solicited local and systemic adverse events in the participant's diary card for up to 7 days after each vaccination. Solicited adverse events (AEs) were tabulated and graded as mild, moderate, or severe.

Figure 12A:
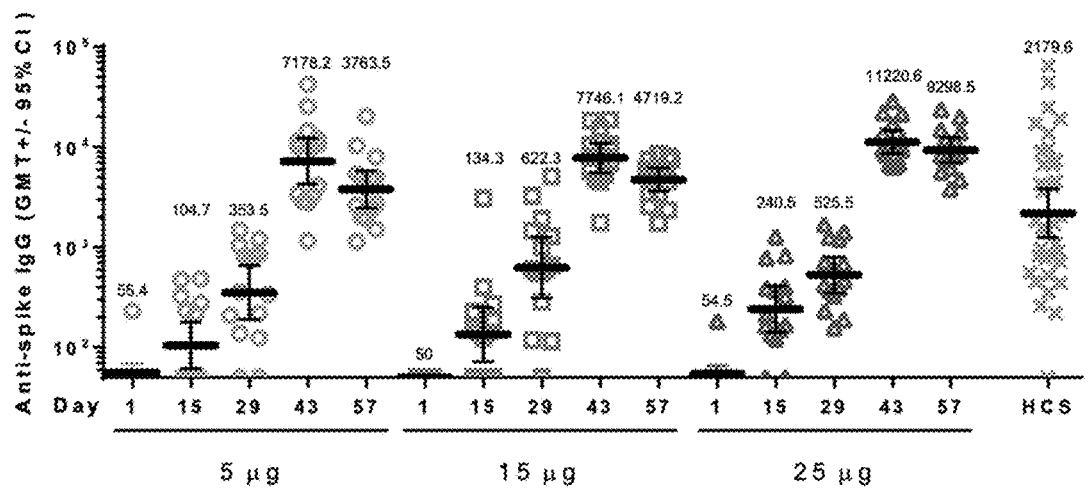
Figure 12B:
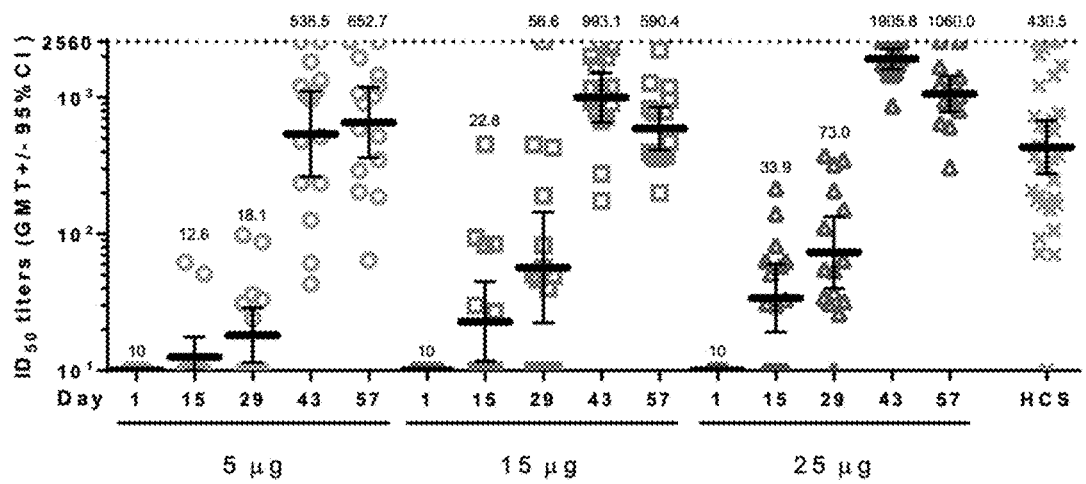
Figure 12C:
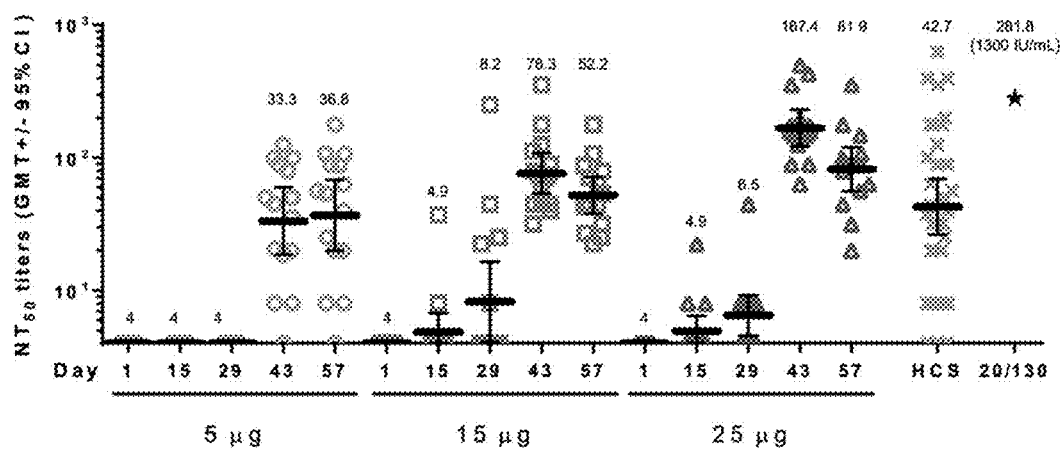

FIGS. 12A-12C shows summary of humoral immune response in the Phase I clinical trial. Sera of participants vaccinated with 5, 15, or 25 μg of MVC-COV1901 were measured for anti-spike IgG by ELISA (FIG. 12A), and neutralization titers were measured by pseudovirus neutralization assay (FIG. 12B) or live virus neutralization assay (FIG. 12C). Human convalescent sera (HCS) from 35 recovered COVID-19 patients were analyzed by the same assays for comparison and NIBSC 20/130 standard was used in the live virus neutralization assay as a standard (asterisk in FIG. 12C). Bars indicate geometric mean titers and error bars indicate 95% confidence intervals.

Figure 13:
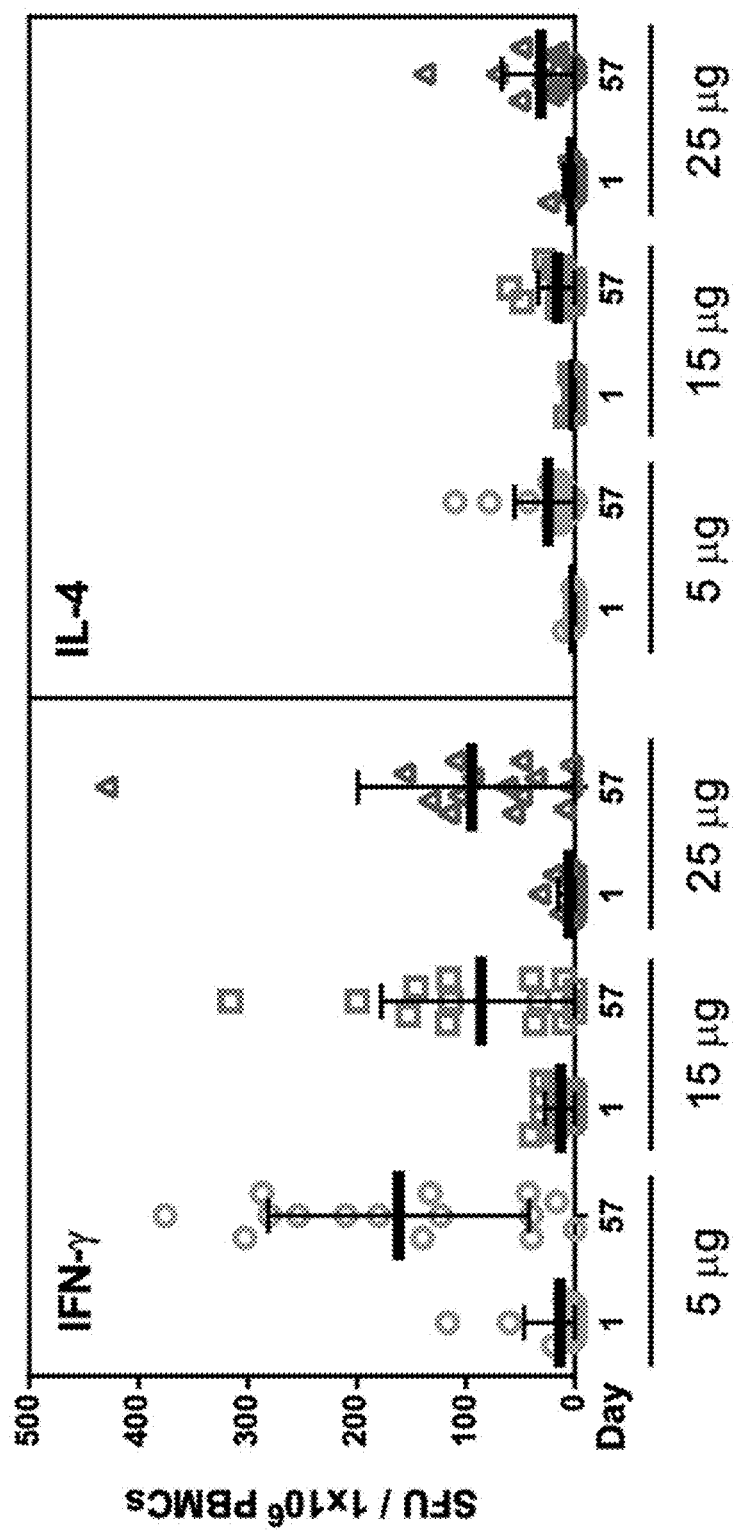

FIG. 13 shows summary of cellular immune response in the Phase I clinical trial. Cells were stimulated with a S1 peptides pool of peptides and incubated at 37° C. for 24-48 hours. Cells stimulated with CD3-2 mAb served as a positive control. IFN-γ (left panel) or IL-4 (right panel) were detected using an ELISpot assay. The mean of spot-forming units (SFU) counted in peptide pool stimulation triplicate was calculated and normalized by subtracting the mean of the negative control replicates (control media). Results were expressed as SFU per million PBMC. Bars indicate the mean values and error bars indicate standard deviations.

Figure 14:
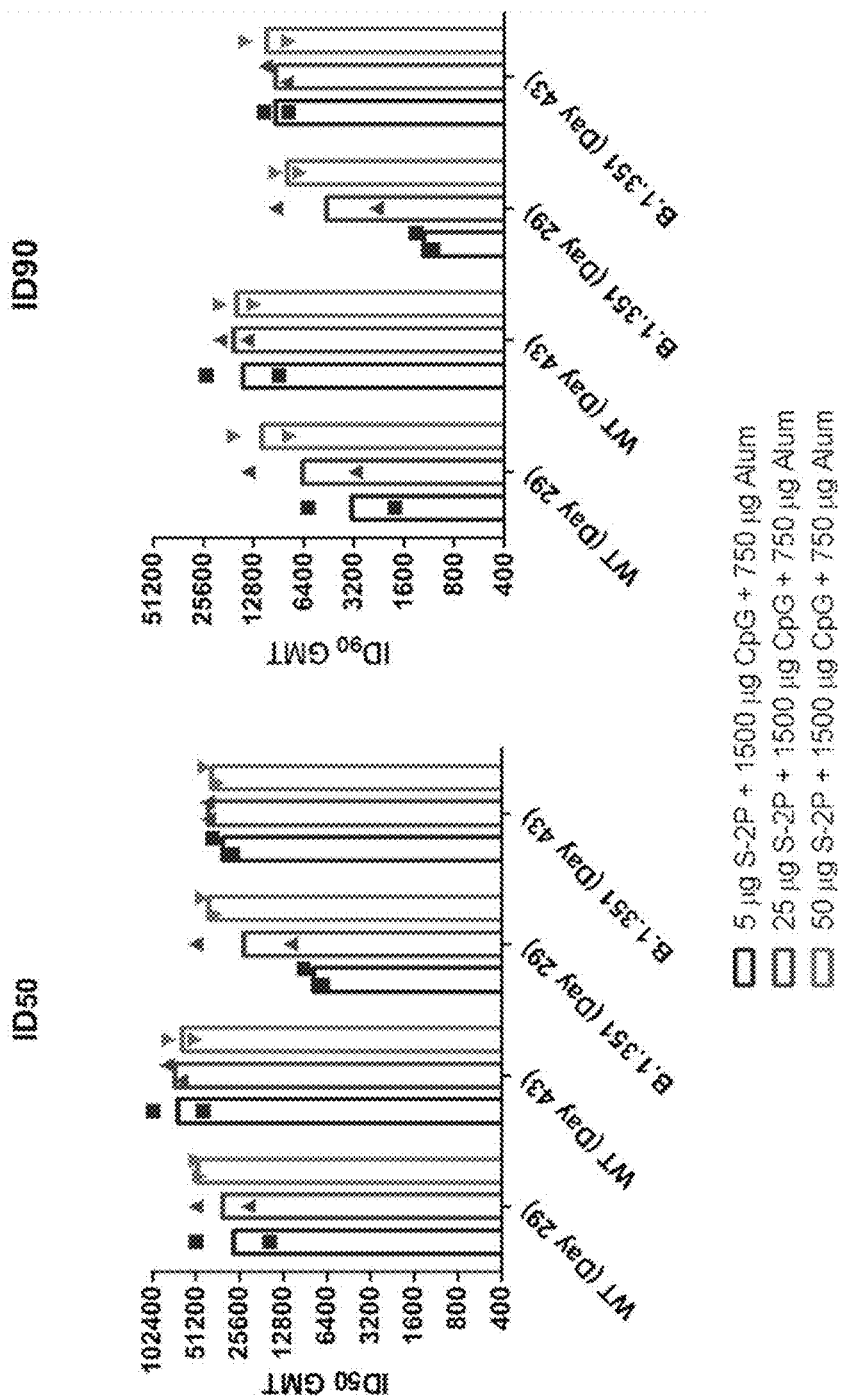

FIG. 14 shows neutralization of SARS-CoV-2 pseudovirus bearing wildtype or B.1.351 (Beta) variant spike proteins by antisera of rats vaccinated with adjuvanted S-2P. Rats were immunized three times at 2 weeks apart with the indicated amounts of adjuvanted S-2P. Antisera from five males were pooled into one sample and those of 5 females were pooled into another sample. This resulted in two pooled samples (N=2) for each dose group. The antisera were harvested two weeks after the second immunization (Day 29) or two weeks after the third immunization (Day 43), pooled as described above and subjected to neutralization assay with pseudovirus expressing SARS-CoV-2 Wuhan wildtype or B.1.351 variant spike protein to determine the $ID_{50}$ and $ID_{90}$ titers of neutralizing antibodies. Results are presented as bars representing geometric mean titers with symbols representing value of each sample.

Figure 15C:
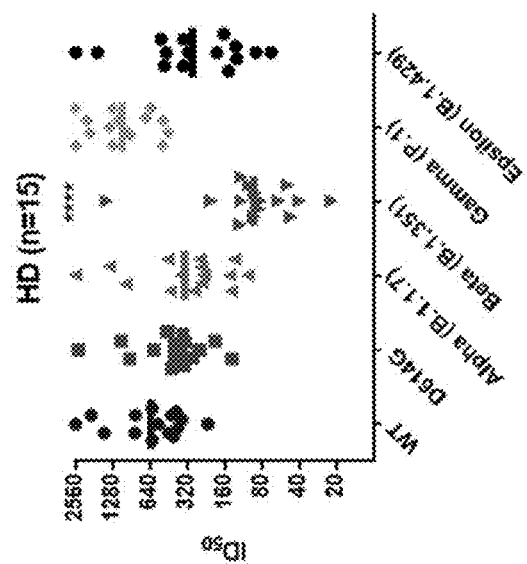
Figure 15B:
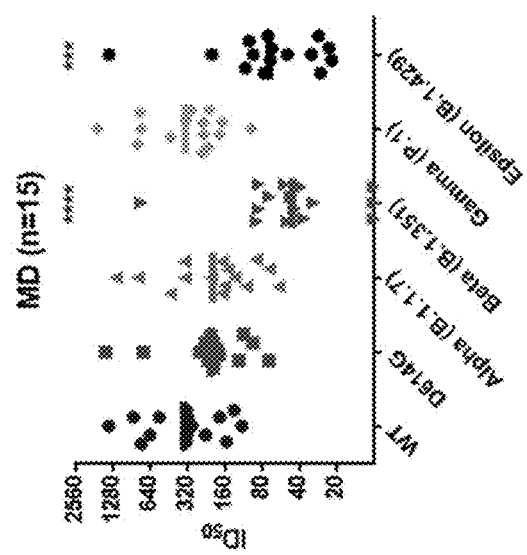
Figure 15A:
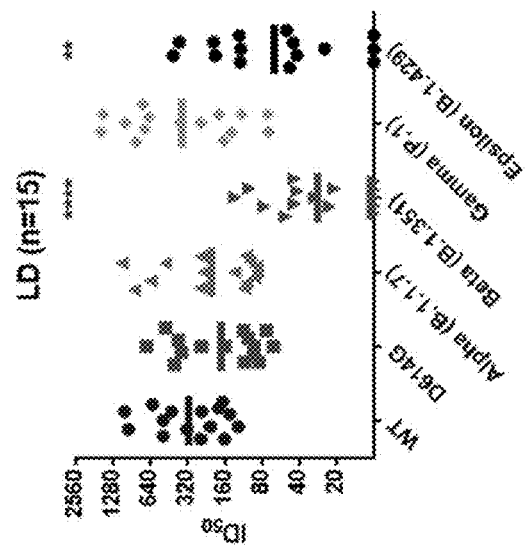

FIGS. 15A-15C show neutralization of SARS-CoV-2 pseudovirus bearing wildtype or variant spike proteins by antisera of clinical trial subjects vaccinated with different does of MVC-COV1901 vaccine. Serum samples from the phase 1 clinical trial of MVC-COV1901 subjects were collected 4 weeks after the second immunization (56 days from the first immunization). $ID_{50}$ neutralizing titers for low dose (LD; FIG. 15A), mid-dose (MD; FIG. 15B), and high dose (HD; FIG. 15C), and all dose groups were measured with pseudovirus neutralization assays. Results are represented with each dot representing individual serum sample neutralizing titer. Kruskal-Wallis with corrected Dunn's multiple comparisons test was performed and statistical significance of variants relative to wildtype is shown above respective column. p<0.01, *p<0.001, ****p<0.0001.

DETAILED DESCRIPTION OF THE PREFERRED EMBODIMENT

The present invention relates to an immunogenic composition against SARS-CoV-2. The immunogenic composition comprises an antigenic recombinant protein and an adjuvant containing an aluminum-containing adjuvant and/or an unmethylated cytosine-phosphate-guanosine (CpG) motif. The antigenic recombinant protein comprises residues 14-1208 of SARS-CoV-2 S protein with proline substitutions at residues 986 and 987 and a "GSAS" substitution at residues 682-685 and a C-terminal T4 fibritin trimerization domain.

In some embodiments, the residues 14-1208 of SARS-CoV-2 S protein with proline substitutions at residues 986 and 987 and a "GSAS" substitution at residues 682-685 comprise an amino acid sequence of SEQ ID NO: 1 or the amino acid sequence at least 90%, 91%, 92%, 93%, 94%, 95%, 96%, 97%, 98%, or 99% to SEQ ID NO: 1.

In some embodiments, the C-terminal T4 fibritin trimerization motif comprises an amino acid sequence of SEQ ID NO: 2 or the amino acid sequence at least 90%, 91%, 92%, 93%, 94%, 95%, 96%, 97%, 98%, or 99% to SEQ ID NO: 2.

In some embodiments, the antigenic recombinant protein comprises an amino acid sequence of SEQ ID NO: 5 or 6 or the amino acid sequence at least 90%, 95%, 96%, 97%, 98%, or 99% to SEQ ID NO: 5 or 6.

In some embodiments, the aluminum-containing adjuvant comprises aluminum hydroxide, aluminum oxyhydroxide, aluminum hydroxide gel, aluminum phosphate, aluminum phosphate gel, aluminum hydroxyphosphate, aluminum hydroxyphosphate sulfate, amorphous aluminum hydroxyphosphate sulfate, potassium aluminum sulfate, aluminum monostearate or a combination thereof.

In some embodiments, a 0.5 ml dose of the immunogenic composition comprises from about 250 to about 500 µg $Al^{3+}$, or about 375 µg $Al^{3+}$.

In some embodiments, the unmethylated CpG motif comprises a synthetic oligodeoxynucleotide (ODN) of SEQ ID NO: 8, SEQ ID NO: 9, SEQ ID NO: 10, SEQ ID NO: 11, SEQ ID NO: 12, SEQ ID NO: 13, or a combination thereof.

In some embodiments, a 0.5 ml dose of the immunogenic composition comprises from about 750 to about 3000 µg of the synthetic oligodeoxynucleotide, or wherein the immunogenic composition comprises about 750 µg, about 1500 µg, or about 3000 µg of the synthetic oligodeoxynucleotide.

The present invention also relates to a method for eliciting an immune response against a severe acute respiratory syndrome coronavirus 2 (SARS-CoV-2) in a subject in need thereof, comprising administering to the subject an effective amount of the immunogenic composition of the present invention.

The present invention also relates to a method for protecting a subject in need thereof from infection with severe acute respiratory syndrome coronavirus 2 (SARS-CoV-2), comprising administering to the subject an effective amount of the immunogenic composition of the present invention.

The present invention also relates to a method for preventing a subject in need thereof from contracting COVID-19 disease, comprising administering to the subject an effective amount of the immunogenic composition of the present invention.

In some embodiments, the immune response comprises production of neutralizing antibodies against SARS-CoV-2 and Th1-skewed immune response.

In some embodiments, the immunogenic composition is administered by intramuscular injection.

The meaning of the technical and scientific terms as described herein can be clearly understood by a person of ordinary skill in the art.

As used herein, the singular form "a", "an", and "the" includes plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters may also be used in oligonucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. A nucleotide is a phosphate ester of a nucleoside.

As used herein, the terms "severe acute respiratory syndrome coronavirus 2 (SARS-CoV-2)" refers to the strain of coronavirus that causes coronavirus disease 2019 (COVID-19). SARS-CoV-2 is a positive-sense single-stranded RNA virus, with a genome size of 29,903 bases. Each SARS-CoV-2 virion is 50-200 nanometres in diameter, with four structural proteins, known as the S (spike), E (envelope), M (membrane), and N (nucleocapsid) proteins. The N protein holds the RNA genome, and the S, E, and M proteins together create the viral envelope. The spike protein is the protein responsible for allowing the virus to attach to and fuse with the membrane of a host cell; specifically, its S1 subunit catalyzes attachment, the S2 subunit fusion.

As used herein, the terms "immunogenic composition against severe acute respiratory syndrome coronavirus 2 (SARS-CoV-2)" refers to a composition for stimulating or eliciting an immune response against a SARS-CoV-2. The immune response includes, but not limited to, production of neutralizing antibodies against SARS-CoV-2 and Th1-skewed immune response.

As used herein, the terms "aluminum-containing adjuvant" refers to an adjuvant including aluminum. In some embodiments, the aluminum-containing adjuvant includes, but not limited to, aluminum hydroxide, aluminum oxyhydroxide, aluminum hydroxide gel, aluminum phosphate, aluminum phosphate gel, aluminum hydroxyphosphate, aluminum hydroxyphosphate sulfate, amorphous aluminum hydroxyphosphate sulfate, potassium aluminum sulfate, aluminum monostearate or a combination thereof. In some embodiments, the aluminum-containing adjuvant is an aluminum-containing adjuvant approved for administration to humans by the FDA. In some embodiments, the aluminum-containing adjuvant is an aluminum hydroxide adjuvant approved for administration to humans by the FDA. In some embodiments, the aluminum-containing adjuvant is an aluminum phosphate adjuvant approved for administration to humans by the FDA.

As used herein, the terms "unmethylated cytosine-phosphate-guanosine (CpG) motif" refers to a CpG-containing oligonucleotide in which the C is unmethylated, and which contributes to a measurable immune response as measured in vitro, in vivo, and/or ex vivo. In some embodiments, the CpG-containing oligonucleotide contains palindromic hexamers following the general formula of: 5'-purine-purine-CG-pyrimidine-pyrimidine-3'. In some preferred embodiments, the unmethylated cytosine-phosphate-guanosine (CpG) motif has an oligonucleotide of SEQ ID NO: 8 (5'-TGACTGTGAACGTTCGAGATGA-3') in which the Cs of the CGs are unmethylated. In some embodiments, the CpG-containing oligonucleotide contains TCG in which the C is unmethylated, and which is from 8 to 100 nucleotides, preferably 8 to 50 nucleotides, or preferably 8 to 25 nucleotides in length. In some preferred embodiments, the unmethylated cytosine-phosphate-guanosine (CpG) motif has an oligonucleotide of SEQ ID NO: 9 (5'-TCGTCGTTTTGTCGTTTTGTCGTT-3') in which the Cs of the TCGs are unmethylated. Examples of the unmethylated cytosine-phosphate-guanosine (CpG) motif further includes, but not limited to, 5'-GGTGCATC-GATGCAGGGG GG-3' (SEQ ID NO: 10), 5'-TC-CATGGACGTTCCTGAGCGTT-3' (SEQ ID NO: 11), 5'-TCGTCGTTCGAACGACGTTGAT-3' (SEQ ID NO: 12), and 5'-TCGTCGACGATCGGC GCGCGCCG-3' (SEQ ID NO: 13). The CpG-containing oligonucleotide described herein are in their pharmaceutically acceptable salt form unless otherwise indicated. In one preferred embodiment, the CpG-containing oligonucleotides are in the sodium salt form.

An "effective amount" or a "sufficient amount" of a substance is that amount sufficient to effect beneficial or desired results, including clinical results, and, as such, an "effective amount" depends upon the context in which it is being applied. In the context of administering an immunogenic composition, an effective amount contains sufficient adjuvant and SARS-CoV-2 S-2P recombinant protein to elicit an immune response. An effective amount can be administered in one or more doses.

The terms "individual" and "subject" refer to mammals. "Mammals" include, but are not limited to, humans, non-human primates (e.g., monkeys), farm animals, sport animals, rodents (e.g., mice and rats) and pets (e.g., dogs and cats).

The term "dose" as used herein in reference to an immunogenic composition refers to a measured portion of the immunogenic composition taken by (administered to or received by) a subject at any one time.

The terms "isolated" and "purified" as used herein refers to a material that is removed from at least one component with which it is naturally associated (e.g., removed from its original environment). The term "isolated," when used in reference to a recombinant protein, refers to a protein that has been removed from the culture medium of the host cell that produced the protein.

"Stimulation" of a response or parameter includes eliciting and/or enhancing that response or parameter when compared to otherwise same conditions except for a parameter of interest, or alternatively, as compared to another condition (e.g., increase in TLR-signaling in the presence of a TLR agonist as compared to the absence of the TLR agonist). For example, "stimulation" of an immune response means an increase in the response. Depending upon the parameter measured, the increase may be from 5-fold to 500-fold or over, or from 5, 10, 50, or 100-fold to 500, 1,000, 5,000, or 10,000-fold.

As used herein the term "immunization" refers to a process that increases a mammalian subject's reaction to antigen and therefore improves its ability to resist or overcome infection.

The term "vaccination" as used herein refers to the introduction of vaccine into a body of a mammalian subject.

"Adjuvant" refers to a substance which, when added to a composition comprising an antigen, nonspecifically enhances or potentiates an immune response to the antigen in the recipient upon exposure.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

Example 1 Preparation of Immunogenic Compositions Against SARS-CoV-2

A plasmid having a polynucleotide encoding the residues 1-1208 of SARS-CoV-2 S protein (Wuhan-Hu-1 strain; GenBank: MN908947) with proline substitutions at residues 986 and 987, a "GSAS" substitution at the furin cleavage site (residues 682-685) (SEQ ID NO: 14) and a C-terminal T4 fibritin trimerization domain (SEQ ID NO: 2), an HRV3C protease cleavage site (SEQ ID NO: 3), an 8× His Tag, and a Twin-Strep Tag (SEQ ID NO: 4) was transfected into ExpiCHO-S cells (Thermo Fisher Scientific, Waltham, MA, USA).

Cell culture was harvested after 6 days, and protein was purified from the supernatant using Strep-Tactin resin (IBA Lifesciences, Göttingen, Germany). HRV3C protease (1% wt/wt) was added to the protein and the reaction was incubated overnight at 4° C. The digested protein was further purified using a Superose 6 16/70 column (GE Healthcare Biosciences, Chicago, IL, USA). The purified SARS-CoV-2 S-2P recombinant protein (SEQ ID NO: 5 or 6) was then formulated with an unmethylated CpG motif (CpG 1018, SEQ ID NO: 8) and/or aluminum-containing adjuvant, such as aluminum hydroxide $(Al(OH)_3)$ or aluminum phosphate $(AlPO_4)$ as the immunogenic compositions against SARS-CoV-2.

Example 2 Immunogenicity of the Immunogenic Compositions Against SARS-CoV-2 in Mice This example provides a description of preclinical studies to assess the immunogenicity of the immunogenic compositions against SARS-CoV-2 obtained from Example 1 in mice.

A. Preliminary Test 1—SARS-CoV-2 S-2P Recombinant Protein Formulated with Aluminum Phosphate Materials and Methods Mouse immunizations. BALB/c mice aged 6-8 weeks (The National Laboratory Animal Center, Taiwan) (N=5/group) were vaccinated with the SARS-CoV-2 S-2P recombinant protein at 0 and 3rd week. SARS-CoV-2 S-2P recombinant protein (a final concentration of 1 μg or 10 μg/mL) diluted in PBS was mixed with aluminum phosphate (to a final concentration of 0.5 mg aluminum/mL). Mice were inoculated with 100 μL intramuscularly (50 μL into each hind leg). Two weeks after the final immunization, sera were collected for measurement of antibody responses.

Pseudovirus production. cDNA encoding spike protein of Wuhan-Hu-1 strain (SEQ ID NO: 7) was synthesized using the QuikChange XL kit (Stratagene, San Diego, CA, USA) and then inserted into CMV/R plasmid. The CMV/R-SARS-CoV-2 spike plasmid was confirmed using sequencing. HEK293T cells were obtained from ATCC and cultured in DMEM supplemented with 10% FBS, 2 mM glutamine, and 1% penicillin/streptomycin at 37° C. and 5% $CO_2$. To produce SARS-CoV-2 pseudoviruses, CMV/R-SARS-CoV-2 spike plasmid was co-transfected into HEK293T cells with packaging plasmid pCMVDR8.2 and transducing plasmid pHR CMV-Luc, using Fugene 6 transfection reagent (Promega, Madison, WI, USA). Seventy-two (72) hours post-transfection, supernatant was collected, filtered, and frozen at −80° C.

Pseudovirus infectivity and neutralization assay. Huh7.5 cells (RRID: CVCL_7927) were cultured in DMEM supplemented with 10% FBS, 2 mM glutamine, and 1% penicillin/streptomycin at 37° C. and 5% $CO_2$. Pseudovirus infectivity was assessed in Huh7.5 cells plated overnight in 96-well black/white isoplates (PerkinElmer, Waltham, MA, USA). Twofold serial dilutions of pseudoviruses were added to resting Huh7.5 cells, in triplicate. After a 2-hour incubation, fresh medium was added. Cells were lysed at 72 hours, and luciferase substrate (Promega) was added. Luciferase activity was measured as relative luciferase units (RLU) at 570 nm on a SpectramaxL (Molecular Devices, San Jose, CA, USA). For neutralization experiments, serial dilutions of mouse sera (1:40, fourfold, eight dilutions) were mixed with various pseudovirus strains, which were previously titered to target 50,000 RLU. Sigmoidal curves, taking averages of triplicates at each dilution, were generated from RLU readings; 50% neutralization titers ($IC_{50}$) were calculated considering uninfected cells as 100% neutralization and cells transduced with only virus as 0% neutralization.

Results

Figure 1:
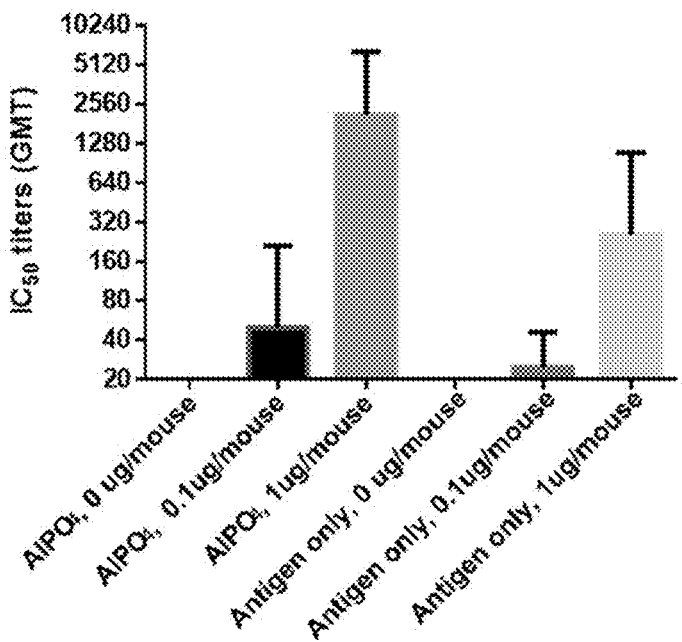
FIG. 1 shows the results from neutralization assays using sera from mice immunized with the SARS-CoV-2 S-2P recombinant protein with or without aluminum phosphate adjuvant.

The results of neutralization assay are shown in FIG. 1. SARS-CoV-2 S-2P recombinant protein (0.1 μg/mouse and 1 μg/mouse) formulated with aluminum phosphate elicited greater neutralization than the recombinant protein (0.1 μg/mouse and 1 μg/mouse) alone. These data demonstrate that aluminum phosphate significantly increase the immunogenicity of the SARS-CoV-2 S-2P recombinant protein as an antigen of a vaccine against coronavirus disease (COVID-19).

B. Preliminary Test 2—SARS-CoV-2 S-2P Recombinant Protein Formulated with the Combination of CpG and Aluminum Hydroxide Materials and Methods Mouse immunizations. BALB/c mice aged 6-8 weeks (The National Laboratory Animal Center, Taiwan) (N=6/group) were vaccinated with the SARS-CoV-2 S-2P recombinant protein at 0 and 3rd week. SARS-CoV-2 S-2P recombinant protein (a final concentration of 10 μg or 50 μg/mL) diluted in PBS was mixed with CpG 1018 (SEQ ID NO: 8) (to a final concentration of 0.1 mg/mL), aluminum hydroxide (to a final concentration of 0.5 mg aluminum/mL), or a combination of CpG 1018 (to a final concentration of 0.1 mg/mL) and aluminum hydroxide (to a final concentration of 0.5 mg aluminum/mL), respectively. Mice were inoculated with 100 μL intramuscularly (50 μL into each hind leg). Two weeks after the final immunization, sera were collected for measurement of antibody responses.

Pseudovirus production, pseudovirus infectivity, and neutralization assay. The methods are described in section A.

Results

Figure 2:
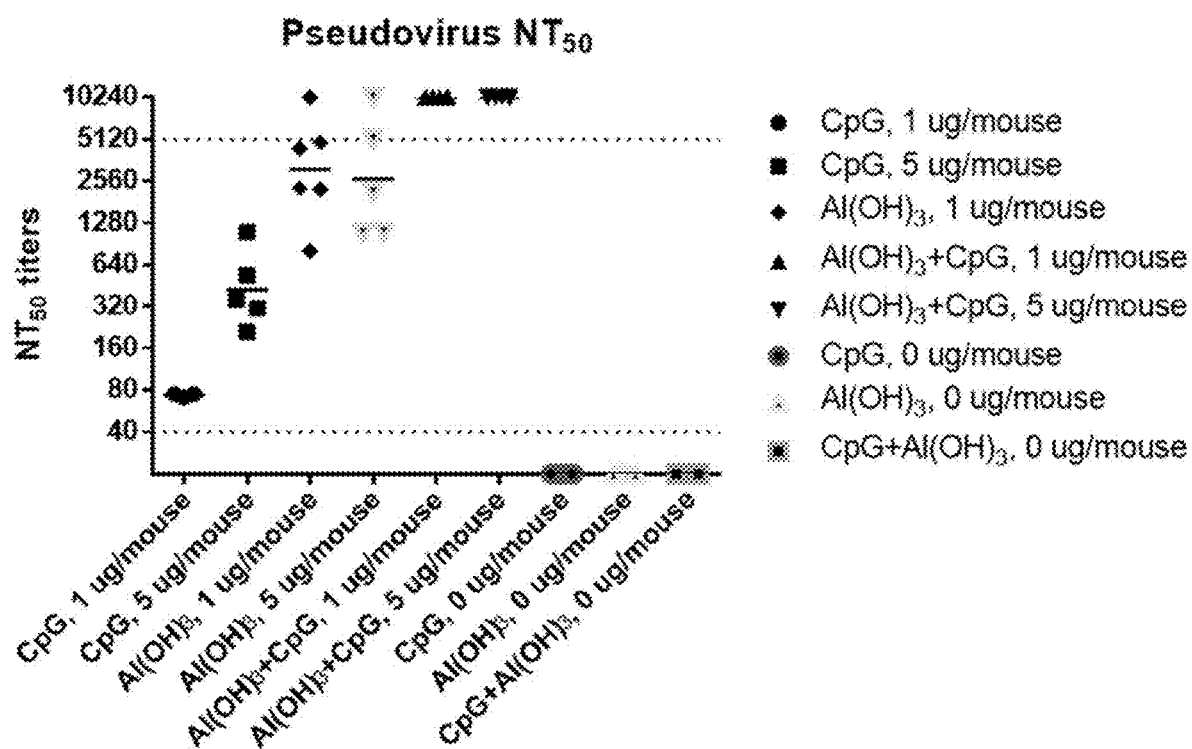
FIG. 2 shows the results from neutralization assays using sera from mice immunized with different formulations of the SARS-CoV-2 S-2P recombinant protein.

The results of neutralization test are shown in FIG. 2. SARS-CoV-2 S-2P recombinant protein formulated with the combination of CpG and aluminum hydroxide elicited the highest neutralizing activity both at a low dose (1 μg/mouse) and a higher dose (5 μg/mouse). In addition, SARS-CoV-2 S-2P recombinant protein (1 μg/mouse) formulated with aluminum hydroxide alone elicited greater neutralization than the recombinant protein (1 μg/mouse and 5 μg/mouse) formulated with CpG alone. The recombinant protein formulated with CpG alone elicited neutralizing activity in a dose-dependent manner. These data demonstrate that CpG and/or aluminum hydroxide significantly increase the immunogenicity of the SARS-CoV-2 S-2P recombinant protein as an antigen of a vaccine against coronavirus disease (COVID-19).

C. Development of Adjuvanted Stable Prefusion SARS-CoV-2 Spike Protein Antigen

Materials and Methods

Pseudovirus production and titration. To produce SARS-CoV-2 pseudoviruses, a plasmid expressing full-length wild-type Wuhan-Hu-1 strain SARS-CoV-2 spike protein (SEQ ID NO: 7) was co-transfected into HEK293T cells with packaging and reporter plasmids pCMVΔ8.91 and pLAS2w.FLuc.Ppuro (RNAi Core, Academia *Sinica*), using TransIT-LT1 transfection reagent (Mirus Bio). Site-directed mutagenesis was used to generate the D614G variant by changing nucleotide at position 23403 (Wuhan-Hu-1 reference strain) from A to G. Mock pseudoviruses were produced by omitting the p2019-nCoV spike (WT). Seventy-two hours post-transfection, supernatants were collected, filtered, and frozen at −80° C. The transduction unit (TU) of SARS-CoV-2 pseudotyped lentivirus was estimated by using cell viability assay in response to the limited dilution of lentivirus. In brief, HEK-293 T cells stably expressing human ACE2 gene were plated on 96-well plate 1 day before lentivirus transduction. For the titering of pseudovirus, different amounts of pseudovirus were added into the culture medium containing polybrene. Spin infection was carried out at 1100×g in 96-well plate for 30 min at 37° C. After incubating cells at 37° C. for 16 hours, the culture media containing virus and polybrene were removed and replaced with fresh complete DMEM containing 2.5 μg/ml puromycin. After treating with puromycin for 48 h, the culture media were removed and cell viability was detected by using 10% AlarmaBlue reagents according to manufacturer's instruction. The survival rate of uninfected cells (without puromycin treatment) was set as 100%. The virus titer (transduction units) was determined by plotting the survival cells versus diluted viral dose.

Pseudovirus-based neutralization assay. HEK293-hAce2 cells ($2\times10^4$ cells/well) were seeded in 96-well white isoplates and incubated for overnight. Sera were heated at 56° C. for 30 min to inactivate complement and diluted in MEM supplemented with 2% FBS at an initial dilution factor of 20, and then twofold serial dilutions were carried out (for a total of 8 dilution steps to a final dilution of 1:5120). The diluted sera were mixed with an equal volume of pseudovirus (1000 TU) and incubated at 37° C. for 1 h before adding to the plates with cells. After the 1 h incubation, the culture medium was replaced with 50 μL of fresh medium. On the following day, the culture medium was replaced with 100 μL of fresh medium. Cells were lysed at 72 h post infections and relative luciferase units (RLU) were measured. The luciferase activity was detected by Tecan i-control (Infinite 500). The 50% and 90% inhibition dilution titers ($ID_{50}$ and $ID_{90}$) were calculated considering uninfected cells as 100% neutralization and cells transduced with only virus as 0% neutralization. Reciprocal $ID_{50}$ and $ID_{90}$ geometric mean titers (GMT) were both determined as $ID_{90}$ titers are useful when $ID_{50}$ titer levels are consistently saturating at the upper limit of detection.

Wild-type SARS-CoV-2 neutralization. The neutralization assay with SARS-CoV-2 virus was conducted as previously reported (Huang et al., J. Clin. Microbiol. 58(8): e01068-e1120, 2020). Vero E6 cells ($2.5 \times 10^4$ cells/well) were seeded in 96-well plates and incubated overnight. Sera were heated at 56° C. for 30 min to inactivate complement and diluted in serum-free MEM at an initial dilution factor of 20, and then further twofold serial dilutions were performed for a total of 11 dilution steps to a final dilution of 1:40,960. The diluted sera were mixed with an equal volume of SARS-CoV-2 virus at 100 $TCID_{50}$/50 μL (hCoV-19/Taiwan/CGMH-CGU-01/2020, GenBank accession MT192759) and incubated at 37° C. for 2 h. The sera-virus mixture was then added to 96-well plate with Vero E6 cells and incubated in MEM with 2% FBS at 37° C. for 5 days. After incubation, cells were fixed by adding 4% formalin to each of the wells for 10 min and stained with 0.1% crystal violet for visualization. Results were calculated with the Reed-Muench method for log 50% end point for $ID_{50}$ and log 90% end point for $ID_{90}$ titers.

Immunization of mice. Female BALB/c and C57BL/6 mice were obtained from the National Laboratory Animal Center, Academia Sinica, Taiwan and BioLASCO Taiwan Co. Ltd. For antigen formulation, SARS-CoV-2 S-2P protein was mixed with either an equal volume of CpG 1018 (SEQ ID NO: 8), aluminum hydroxide, PBS, or CpG 1018 plus aluminum hydroxide. Mice aged 6-9 weeks were immunized twice (50 μL intramuscularly in each of the left and right quadriceps femoris muscles per mouse) at 3 weeks apart as previously described (Pallesen et al., Proc. Natl. Acad. Sci. USA, 114(35): E7348-E7357, 2017). Total serum anti-S IgG and anti-RBD IgG titers were detected with direct ELISA using custom 96-well plates coated with S-2P antigen and an E. coli-expressed fragment of the S protein containing RBD region, respectively.

Cytokine assays. Two weeks after the second injection, mice were euthanized and splenocytes were isolated and stimulated with S-2P protein (2 μg/well) as previously described (Lu et al. Immunology, 130(2): 254-261, 2010). For detection of IFN-γ, IL-2, IL-4, and IL-5, the culture supernatant from the 96-well microplates was harvested to analyze the levels of cytokines by ELISA using Mouse IFN-γ Quantikine ELISA Kit, Mouse IL-2 Quantikine ELISA Kit, Mouse IL-4 Quantikine ELISA Kit, and Mouse IL-5 Quantikine ELISA Kit (R&D System). The OD450 values were read by Multiskan GO (Thermo Fisher Scientific).

Dose range finding study for single- and repeat-dose intramuscular injection (IM) in Sprague Dawley (SD) rats. Crl:CD Sprague Dawley (SD) rats were obtained from BioLASCO Taiwan Co. Ltd. Animal studies were conducted in the Testing Facility for Biological Safety, TFBS Bioscience Inc., Taiwan. SD rats aged 6-8 weeks were immunized with 5 μg, 25 μg or 50 μg of S-2P adjuvanted with either 1500 μg CpG 1018 alone or 750 μg CpG 1018 combined with 375 μg aluminum hydroxide. The test article or vehicle control was administered intramuscularly (0.25 mL/site, 2 sites of quadriceps femoris muscle) to each rat on Day 1 (for single-dose study) and Day 15 (for repeat-dose study). The observation period was 14 days (for single-dose study) and 28 days (for repeat-dose study). Parameters evaluated included clinical signs, local irritation examination, moribundity/mortality, body temperature, body weights, and food consumption during the in-life period. Blood samples were taken for hematology, including coagulation tests and serum chemistry. All animals were euthanized and necropsied for gross lesion examination, organ weights, and histopathology evaluation on injection sites and lungs.

Statistical analysis. For neutralization assays, geometric mean titers are represented by the heights of bars with 95% confidence intervals represented by the error bars. For cytokine and rat data, heights of bars or symbols represent means with SD represented by error bars. Dotted lines represent lower and upper limits of detection. Analysis package in Prism 6.01 (GraphPad) was used for statistical analysis. The data were compared at the same S-2P dose level with different adjuvant or at the same adjuvant system with varying antigen dose. Kruskal-Wallis with corrected Dunn's multiple comparisons test was used for non-parametric test between more than 2 experimental groups. Mann-Whitney U-test was used to compare two experimental groups. For correlation between antibody titers and neutralization titers, Spearman's rank correlation coefficient was used. *$p<0.05$, $p<0.01$, *$p<0.001$.

Results

Figure 3:
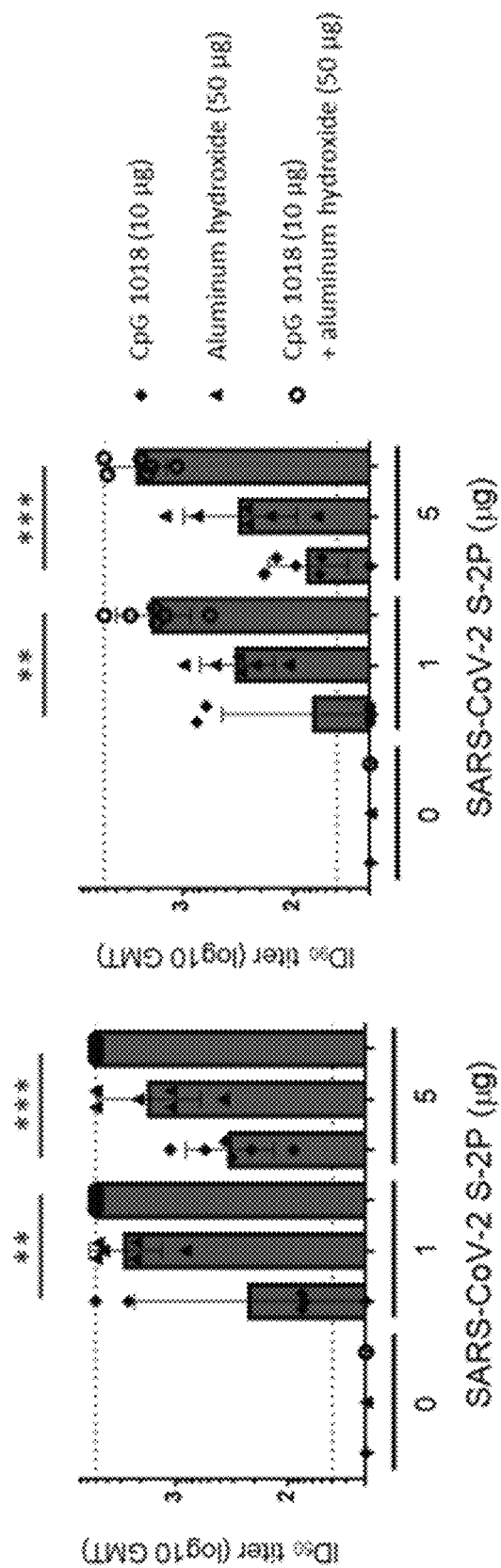
FIG. 3 shows induction of neutralizing antibodies by CpG 1018 and aluminum hydroxide-adjuvanted SARS-CoV-2 S-2P at 2 weeks post-second injection. BALB/c mice (N=6 per group) were immunized with 2 dose levels of Chinese hamster ovary (CHO) cell-expressed SARS-CoV-2 S-2P adjuvanted with CpG 1018, aluminum hydroxide or a combination of both 3 weeks apart and the antisera were harvested at 2 weeks after the second injection. The antisera were subjected to neutralization assay with pseudovirus expressing SARS-CoV-2 spike protein to determine the $ID_{50}$ (left) and $ID_{90}$ (right) titers of neutralization antibodies. $p<0.01$, *$p<0.001$.

Induction of potent neutralizing antibodies by CpG 1018 and aluminum hydroxide-adjuvanted S-2P. To facilitate establishment of stable clones for clinical studies and commercial production, the ExpiCHO system was used as the expression system of S-2P antigen. The S-2P proteins produced in CHO cells and their structure displayed typical spike trimers under cryo-EM, resembling that of 293-expressed SARS-CoV-2 S protein (Wrapp et al., Science, 367(6483): 1260-1263, 2020), suggesting that CHO cells are feasible in production of S-2P. Next, the potential of Th1-biasing CpG 1018 for clinical use was examined. Aluminum hydroxide (hereafter abbreviated as alum) was tested along with CpG 1018 since alum has been characterized to enhance the potency of CpG adjuvant when used in combination while also retaining the property of inducing Th1 responses (Thomas et al., Hum. Vaccin., 5(2): 79-84, 2009). The pseudovirus neutralization assay was performed with sera drawn either 3 weeks after the first injection or 2 weeks after the second injection. At 3 weeks after the first injection, neutralizing activities were already observed when mice were immunized with both 1 and 5 μg of S-2P with CpG 1018 and alum. At 2 weeks after the second injection, reciprocal inhibition dilution 50 ($ID_{50}$) GMT of 245, 3109, and 5120 were obtained with immunization of 1 μg S-2P adjuvanted with CpG 1018, alum, and with both CpG 1018 and alum, respectively (FIG. 3). Similar trends were observed at 5 μg of S-2P in both BALB/c (FIG. 3) and C57BL/6 mice.

Figure 4:
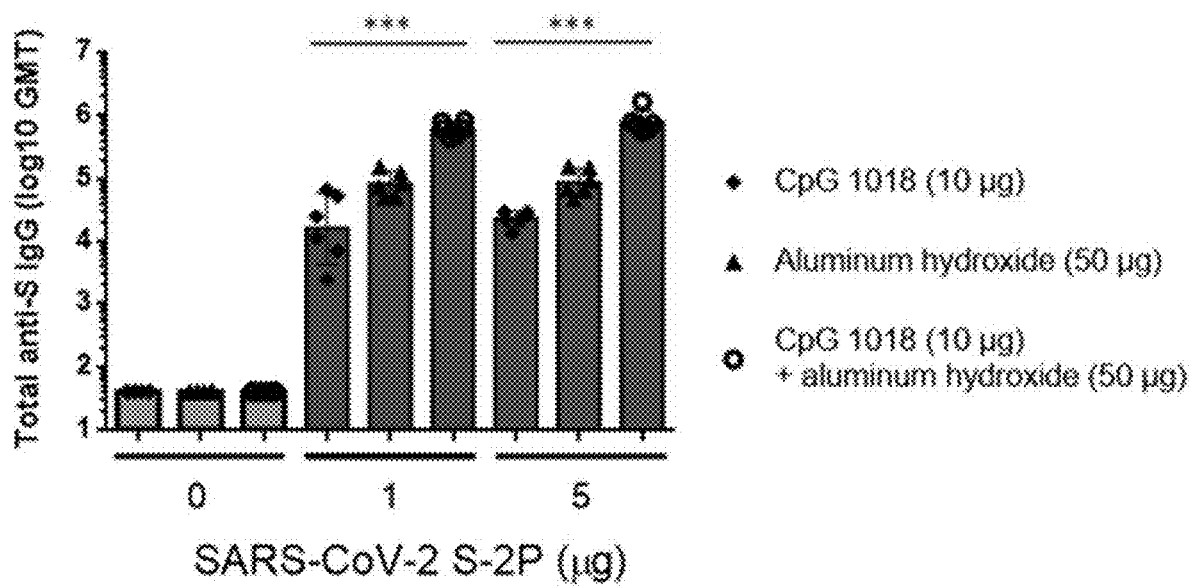
FIG. 4 shows total anti-S IgG titers in mice immunized with S-2P with adjuvants. Sera from BALB/c mice in FIG. 3 (N=6 per group) immunized with 0, 1 or 5 μg of S-2P with CpG 1018, aluminum hydroxide or a combination of both were quantified for the total amount of anti-S IgG in an enzyme linked immunosorbent assay (ELISA). ***$p<0.001$.

Sera from these mice were then examined for the amount of anti-S IgG. CpG 1018 in combination with alum produced significantly higher titers of anti-S IgG compared to CpG 1018 alone (FIG. 4). To confirm the activities of the antibodies against the critical receptor-binding domain (RBD) of the S protein, immune sera were examined for anti-RBD IgG and the results were similar to that of the anti-S IgG with S-2P in combination with both CpG 1018 and alum induced the highest amount of IgG titer. There was a moderate correlation between anti-S IgG and anti-RBD IgG titers as shown by Spearman's rank correlation coefficient of 0.6486. The immune sera were further tested for their neutralization capabilities against wild-type SARS-CoV-2 in a neutralization assay. S-2P was able to inhibit SARS-CoV-2 at a concentration of 1 μg, although at lower potency than that of pseudovirus (FIG. 3, FIG. 5). The reciprocal $ID_{50}$ GMT of 1 μg S-2P in the presence of CpG 1018, alum, and with both CpG 1018 and alum were approximately 60, 250, and 1500, respectively (FIG. 5). Pseudovirus carrying the current dominant D614G variant spike was also generated and neutralizing antibodies from mice immunized with S-2P with CpG 1018 and alum were effective against both pseudoviruses carrying the wild-type D614 and mutant D614G versions of spike proteins (FIG. 6). Neutralization titers of wild-type virus and pseudovirus and total anti-S IgG titers were all found to be highly correlated with Spearman's rank correlation coefficients greater than 0.8.

CpG 1018 induced Th1 immunity. To identify whether CpG 1018 could induce Th1 responses in the vaccine-adjuvant system, cytokines involved in Th1 and Th2 responses were measured in splenocytes from mice immunized with S-2P with alum, CpG 1018, or combination of the two. As expected, S-2P adjuvanted with alum induced limited amounts of IFN-γ and IL-2, the representative cytokines of Th1 response. In contrast, significant increases in IFN-γ and IL-2 were detected most strongly in high antigen dose plus CpG 1018 and alum. For Th2 response, while the levels of IL-4, IL-5 and IL-6 increased in the presence of alum and S-2P, addition of CpG 1018 to alum suppressed the levels of IL-5 and IL-6. IFN-γ/IL-4, IFN-γ/IL-5, and IFN-γ/IL-6 ratios are strongly indicative of a Th1-biased response and were increased by approximately 36-, 130-, and two-fold, respectively, in the presence of S-2P combined with CpG 1018 and alum (FIG. 7). These results suggested that the effect of CpG 1018 is dominant over alum in directing the cell-mediated response towards Th1 response, while retaining high antibody levels.

S-2P did not result in systemic adverse effects in rats. To elucidate the safety and potential toxicity of the vaccine candidate, 5 μg, 25 μg or 50 μg of S-2P adjuvanted with 1500 μg CpG 1018 or 750 μg CpG 1018 combined with 375 μg alum were administered to SD rats for single-dose and repeat-dose studies. No mortality, abnormality of clinical signs, differences in body weight changes, body temperature, nor food consumption were observed in either gender that could be attributed to S-2P (with or without adjuvant) with single dose administration. Increased body temperature at 4-h or 24-h after dosing was found in both genders of single-dose study and repeat-dose study; however, these temperature changes were moderate and were recovered after 48-h in both genders of all treated groups including controls (PBS). No gross lesions were observed in organs of most of the male and female rats with single-dose and two-dose administration, except for one male rat which was deemed to be non-vaccine-related. In conclusion, S-2P protein, with CpG 1018 or CpG 1018 with alum as adjuvants administrated intramuscularly once or twice to SD rats did not induce any systemic adverse effect.

The results show that in mice, two injections of a subunit vaccine consisting of the prefusion spike protein (S-2P) adjuvanted with CpG 1018 and alum were effective in inducing potent neutralization activity against both pseudovirus expressing wild-type and D614G variant spike proteins, and wild-type SARS-CoV-2. The combination of S-2P with CpG 1018 and alum elicited Th1-dominant immune responses with high neutralizing antibody levels in mice and showed no major adverse effects in rats. Therefore, the inventors have demonstrated in this Example that the S-2P combined with adjuvant CpG 1018 in combination with alum induced potent Th1-biased immune responses to prevent wild-type virus infections while retaining high antibody levels that show cross-neutralization of variant viruses. Therefore, the immunogenic compositions against SARS-CoV-2 of the present invention serves as an ideal vaccine candidate in alleviating the burden of the global COVID-19 pandemic.

Example 3 Protection from SARS-CoV-2 Challenge by the Immunogenic Compositions Against SARS-CoV-2 in Hamster Materials and Methods Pseudovirus-based neutralization assay and IgG ELISA. Lentivirus expressing the Wuhan-Hu-1 strain SARS-CoV-2 spike protein was constructed and the neutralization assay performed as described in Example 2. Briefly, HEK293-hACE2 cells were seeded in 96-well white isoplates and incubated overnight. Sera from vaccinated and unvaccinated hamsters were heat-inactivated and diluted in MEM supplemented with 2% FBS at an initial dilution factor of 20, and then 2-fold serial dilutions were carried out for a total of 8 dilution steps to a final dilution of 1:5120. The diluted sera were mixed with an equal volume of pseudovirus (1,000 TU) and incubated at 37° C. for 1 hour before adding to the plates with cells. Cells were lysed at 72 hours post-infection and relative luciferase units (RLU) was measured. The 50% and 90% inhibition dilution titers ($ID_{50}$ and $ID_{90}$) were calculated referencing uninfected cells as 100% neutralization and cells transduced with only virus as 0% neutralization. Total serum anti-S IgG titers were detected with direct ELISA using custom 96-well plates coated with S-2P antigen.

Immunization and challenge of hamsters. Female golden Syrian hamsters aged 6-9 weeks old on study initiation were obtained from the National Laboratory Animal Center (Taipei, Taiwan). The hamsters were randomized from different litters into four groups (n=10 for each group): hamsters were vaccinated intramuscularly with 2 injections of vehicle control (PBS), 1 or 5 μg of S-2P protein adjuvanted with 150 μg CpG 1018 and 75 μg aluminum hydroxide (alum), or adjuvant alone at 3 weeks apart. The hamsters were bled at 2 weeks after the second immunization via submandibular vein to confirm presence of neutralizing antibodies. Hamsters were challenged at 4 weeks after the second immunization with $1\times10^4$ PFU of SARS-CoV-2 TCDC #4 (hCoV-19/Taiwan/4/2020, GISAID Accession ID: EPI_ISL_411927) intranasally in a volume of 100 μL per hamster. The hamsters were divided into two cohorts to be euthanized on 3 and 6 days after challenge for necropsy and tissue sampling. Body weight and survival rate for each hamster were recorded daily after infection. On days 3 and 6 after challenge, hamsters were euthanized by carbon dioxide. The right lung was collected for viral load determination (RNA titer and $TCID_{50}$ assay). The left lung was fixed in 4% paraformaldehyde for histopathological examination.

Quantification of viral titer in lung tissue by cell culture infectious assay ($TCID_{50}$). The middle, inferior, and post-caval lung lobes of hamsters were homogenized in 600 l of DMEM with 2% FBS and 1% penicillin/streptomycin using a homogenizer. Tissue homogenate was centrifuged at 15,000 rpm for 5 minutes and the supernatant was collected for live virus titration. Briefly, 10-fold serial dilutions of each sample were added onto Vero E6 cell monolayer in quadruplicate and incubated for 4 days. Cells were then fixed with 10% formaldehyde and stained with 0.5% crystal violet for 20 minutes. The plates were washed with tap water and scored for infection. The fifty-percent tissue culture infectious dose ($TCID_{50}$)/mL was calculated by the Reed and Muench method (Reed and Muench, American Journal of Epidemiology, 27(3): 493-497, 1938).

Real-time RT-PCR for SARS-CoV-2 RNA quantification. To measure the RNA levels of SARS-CoV-2, specific primers targeting 26,141 to 26,253 region of the envelope (E) gene of SARS-CoV-2 genome were used in a TaqMan real-time RT-PCR method (Corman et al., Eurosurveillance. 25(3): 2000045, 2020). Forward primer E-Sarbeco-F1 5'-ACAGGTACGTTAATAGTTAATAGCGT-3' (SEQ ID NO: 15) and the reverse primer E-Sarbeco-R2 5'-ATATTGCAGCAGTACGCACACA-3' (SEQ ID NO: 16), in addition to the probe E-Sarbeco-P1 5'-FAM-ACACTAGCCATCCTTACTGCGCTTCG-BBQ-3' (SEQ ID NO: 17) were used. A total of 30 μL RNA solution was collected from each lung sample using RNeasy Mini Kit (QIAGEN, Germany) according to the manufacturer's instructions. Five (5) μL of RNA sample was added into a total 25 μL mixture of the Superscript III one-step RT-PCR system with Platinum Taq Polymerase (Thermo Fisher Scientific, USA). The final reaction mix contained 400 nM forward and reverse primers, 200 nM probe, 1.6 mM of deoxyribonucleoside triphosphate (dNTP), 4 mM magnesium sulfate, 50 nM ROX reference dye, and 1 μL of enzyme mixture. Cycling conditions were performed using a one-step PCR protocol: 55° C. for 10 min for first-strand cDNA synthesis, followed by 3 min at 94° C. and 45 amplification cycles at 94° C. for 15 sec and 58° C. for 30 sec. Data was collected and calculated by Applied Biosystems 7500 Real-Time PCR System (Thermo Fisher Scientific, USA). A synthetic 113-bp oligonucleotide fragment was used as a qPCR standard to estimate copy numbers of the viral genome. The oligonucleotides were synthesized by Genomics BioSci and Tech Co. Ltd. (Taipei, Taiwan).

Results

Hamsters as SARS-CoV-2 virus challenge model. To develop a SARS-CoV-2 virus challenge model in hamsters for the S2-P vaccine, an initial study was conducted to determine the optimal dose of virus for the challenge experiments. Unvaccinated hamsters were inoculated with $10^3$, $10^4$, or $10^5$ PFU of SARS-CoV-2 and euthanized on Day 3 or 6 after infection for tissue sampling. Following infection of $10^3$ to $10^5$ PFU of SARS-CoV-2, the hamsters exhibited dose-dependent weight loss. Hamsters infected with $10^3$ PFU gained weight while $10^4$ and $10^5$ PFU-infected hamsters experienced progressively severe weight loss at 6 days post-infection (dpi). However, there were no significant differences between levels of viral genome RNA and viral titer measured in $10^3$ to $10^5$ PFU of SARS-CoV-2-infected hamsters at 3 and 6 dpi. All dosages of virus resulted in elevated lung pathology, even at $10^3$ PFU where the animals did not experience weight loss. There was also no virus inoculation dose-dependent effect on lung pathology scores and lung viral load. Therefore $10^4$ PFU of virus was used for virus challenge studies as it provides an adequate balance between clinical signs and virus titer for inoculation.

Administration of S-2P adjuvanted with CpG 1018 and aluminum hydroxide to hamsters induced high levels of neutralizing antibodies. Hamsters were divided into four groups receiving two immunizations at 21 days apart of either vehicle control (PBS only), adjuvant alone, low dose (LD) or high dose (HD) of S-2P in combination with CpG 1018 and aluminum hydroxide (S-2P+CpG 1018+alum). No differences in body weight changes were observed after vaccination among the four groups. Fourteen days after the second immunization, high level of neutralizing antibody titers were found in both LD and HD groups with ninety-percent inhibition dilution ($ID_{90}$) geometric mean titer (GMT) of 2,226 and 1,783, respectively (FIG. 8A). Anti-S IgG antibody levels were high enough that several individual samples reached the upper threshold of detection, with GMTs of LD and HD groups of U.S. Pat. Nos. 1,492,959 and 1,198,315, respectively (FIG. 8B). In general, even at a low dose, S-2P+CpG 1018+alum induced potent levels of immunogenicity in hamsters.

Adjuvanted S-2P protected hamsters from clinical signs and viral load after SARS-CoV-2 challenge. Four (4) weeks after the second immunization, hamsters were challenged with $10^4$ PFU of SARS-CoV-2 virus and body weights were tracked up to 3 or 6 days post infection (dpi). Groups of animals were sacrificed on 3 or 6 dpi for viral load and histopathology analyses. LD and HD vaccinated groups did not show weight loss up to 3 or 6 days after virus challenge and instead gained 5 and 3.8 g of mean weight at 6 dpi, respectively. The protective effect was most significant at 6 dpi in both vaccinated groups, while vehicle control and adjuvant only groups experience significant weight loss. Lung viral load measured by viral RNA and $TCID_{50}$ assays showed that both viral RNA and viral titer decreased significantly at 3 dpi in vaccinated hamsters and dropped to below the lower limit of detection at 6 dpi (FIGS. 9A-9B). Note that viral load, especially viral titer measured by $TCID_{50}$ dropped noticeably at 6 dpi in control and adjuvant only groups due to hamsters' natural immune response (FIGS. 9A-9B). Lung sections were analyzed and pathology scoring was tabulated (FIG. 10). There were no differences at 3 dpi between control and experimental groups; however, at 6 dpi, the vehicle control and adjuvant only groups had significantly increased lung pathology including extensive immune cell infiltration and diffuse alveolar damage, compared to the HD antigen/adjuvant immunized groups (FIG. 10). These results showed that S-2P+CpG 1018+alum induced a robust immune response that was able to suppress viral load in lungs and prevent weight loss and lung pathology in infected hamsters.

All of the hamsters in the S-2P+CpG 1018+alum-immunized groups were protected with significantly reduced lung pathology (generally graded minimal to mild, with a mean score of 1.72 in LD and HD groups), in contrast to diffuse alveolar damage (graded moderate to severe, with a mean score of 4.09 in vehicle and adjuvant control groups) caused by the virus in the lungs of hamsters, in the control groups at 6 dpi. The significance of this study lies not only in the demonstration of in vivo efficacy, but also in safety. The viral challenge study allowed for the assessment of risk of disease enhancement with the vaccine candidate. The histopathology scores of the immunized groups have not differed from the non-challenged animals, indicative of a lack of vaccine-enhanced pathology. The result of the study in this Example provides more data that supports progression of the vaccine candidate's clinical development.

Example 4 Safety and Immunogenicity of a CpG-Adjuvanted S-2P Subunit Vaccine "MVC-COV1901" in Humans This Example provides a Phase I study conducted in healthy, human subjects to assess safety and immunogenicity of a SARS-CoV-2 subunit vaccine (i.e., the immunogenic composition of the present invention). The SARS-CoV-2 subunit vaccine, which is referred to herein as "S-2P+CpG 1018+alum" or "MVC-COV1901", is described in greater detail in Example 1.

Vaccines. MVC-COV1901 is formulated in with three different dosages of SARS-CoV-2 Spike (S) protein with CpG 1018 and aluminum hydroxide as adjuvants. Each MVC-COV1901 vaccine contains 5, 15, or 25 μg of S-2P adjuvanted with 750 μg of CpG 1018 and 375 μg (Al equivalent to weight) of aluminum hydroxide, administered as a single 0.5 mL intramuscular (IM) injection.

Participant. The study aimed to enroll 45 subjects. Eligible participants were healthy adults 20 to 49 years of age. Eligibility was determined based on medical history, physical examination, laboratory tests, and investigators' clinical judgment. Exclusion criteria included a history of known potential exposure to SARS CoV-1 or 2 viruses, having received any other COVID-19 vaccine, impaired immune function, history of autoimmune disease, uncontrolled HIV, HBV, or HCV infection, abnormal autoantibody tests, febrile or acute illness within 2 days of first dose, and acute respiratory illness within 14 days of first dose.

Study Design. This study is a phase I prospective, open-labeled, single-center study to evaluate the safety and immunogenicity of the SARS-CoV-2 vaccine MVC-COV1901. This study was a dose escalation study with three separate groups of participants 20 to 49 years of age. Each sub-phase consisted of 15 participants. The three different dose levels employed were 5, 15, and 25 μg of S-2P protein for cohort 1a, 1b, and 1c, respectively. The vaccination schedule consisted of two doses, administered by IM injection in the deltoid muscle of the non-dominant arm 28 days apart, on Day 1 and Day 29.

Cohort 1a: Four sentinel participants were to be recruited to receive vaccine with 5 μg of S-2P to evaluate the preliminary safety data of the vaccine. If no≥Grade 3 adverse event (AE) or serious adverse event (SAE) occurred within 7 days after the first dose in the 4 sentinel participants, dosing of the remaining participants in Phase 1a and Phase 1b would proceed.

Cohort 1b: Another 4 sentinel participants were to be enrolled to receive vaccine with 15 μg of S-2P. If no≥Grade 3 AE or SAE occurred within 7 days after the first dose in the 4 sentinel participants, dosing of the remaining participants in Phase 1b and Phase 1c would proceed.

Cohort 1c: Another 4 sentinel participants would be enrolled to receive vaccine with 25 μg of S-2P. If no≥Grade 3 AE or SAE occurred within 7 days after the first dose in the 4 sentinel participants, dosing of the remaining participants in Phase 1c would proceed.

Vital signs and electrocardiogram (ECG) were performed before and after vaccination. Participants were observed for at least 30 min after each dose to identify any immediate AEs, and were asked to record solicited local (pain, erythema, swelling/induration) and systemic (fever, myalgia, malaise/fatigue, nausea/vomiting, diarrhea) AEs in the participant's diary card for up to 7 days after each dose. Unsolicited AEs were recorded for 28 days following each dose; all other AEs, SAEs and adverse events of special interest (AESIs) were recorded throughout the study period (approximately 7 months). Serum samples were collected for hematology, biochemistry and immunology evaluation.

The immunogenicity endpoints were to evaluate neutralizing antibody titers and binding antibody titers at 14 days (Day 15) and 28 days (Day 29) after first and at 14 days (Day 43) and 28 days (Day 57) after second dose, as well as 90 days and 180 days after the second dose. Convalescent serum specimens from 35 recovered COVID-19 patients (Mitek COVID-19 Panel 1.1 and COVID-19 Panel 1.4 obtained from Access Biologicals LLC, Vista, CA, USA) were also tested. Cellular immune responses were evaluated at 28 days after the second dose by IFN-γ ELISpot and IL-4 ELISpot.

SARS-CoV-2 Spike-Specific Immunoglobulin G (IgG): Total serum anti-Spike IgG titers were detected with direct enzyme-linked immunosorbent assay (ELISA) using customized 96-well plates coated with S-2P antigen.

SARS-CoV-2 Pseudovirus Neutralization Assay: Serial dilutions of the samples to be tested were performed (initial dilution of 1:20 followed by two-fold dilutions to a final dilution of 1:2560). The diluted serum was mixed with an equal volume of pseudovirus (1000 TU) and incubated before adding to the plates with HEK293-hAce2 cells ($1 \times 10^4$ cells/well). The amount of pseudovirus entering the cells was calculated by lysing and measuring the relative luciferase units (RLU). Fifty percent inhibition dilution (concentration) titers ($ID_{50}$) were calculated considering uninfected cells as 100% neutralization and cells transduced with virus as 0% neutralization and reciprocal $ID_{50}$ geometric mean titers (GMT) were both determined.

Wild-Type SARS-CoV-2 Neutralization Assay. SARS-CoV-2 virus (hCoV-19/Taiwan/CGMH-CGU-01/2020, GenBank accession MT192759) was titrated to obtain $TCID_{50}$ and Vero E6 cells ($2.5 \times 10^4$ cells/well) were seeded in 96-well plates and incubated. The sera underwent two-fold dilutions with the final dilution being 1:8192, and the diluted sera were mixed with equal volume of viral solution containing 100 $TCID_{50}$. The serum-virus mixture was incubated and then added to the plates containing the Vero E6 cells, followed by further incubation. The neutralizing titer was defined as the reciprocal of the highest dilution capable of inhibiting 50% of cytopathic effect (CPE $NT_{50}$), which was calculated in using the Reed-Muench method. The National Institute for Biological Standards and Control (NIBSC; Potters Bar, UK) reference serum sample 20/130, was analyzed using the same validated assays as a comparator.

Cellular Immune Response. The number of antigen-specific IFN-γ or IL-4 secreting spot forming units (SFU) were determined by ELISpot assays. Cryopreserved peripheral blood mononuclear cells (PBMC) were rapidly thawed and allowed to rest overnight. Cells were dispensed at $1 \times 10^5$ cells per well for IFN-γ ELISpot assay (Human IFN-γ ELISpot Kit, Mabtech, Stockholm, Sweden) or $2 \times 10^5$ cells per well for IL-4 ELISpot assay (Human IFN-γ ELISpot Kit, Mabtech, Stockholm, Sweden). Cells were stimulated with a pool of peptides consisting mainly of 15-mer sequences with 11 amino acids overlap, covering the N-terminal S1 domain of the S protein of SARS-CoV-2 (PepTivator SARS-CoV-2 Prot S1, Miltenyi Biotec) and incubated at 37° C. for 24-48 hours. Cells stimulated with CD3-2 mAb served as the positive control. IFN-γ or IL-4 release were detected following the manuals and the spots were counted using the CTL automatic ELISpot reader. The mean SFU counted in peptide pool stimulation triplicate was calculated and normalized by subtracting the mean of the negative control replicates (control media). Results were expressed as SFU per million PBMC.

Statistical Analysis. Safety analyses were performed on the total vaccinated group (TVG) population who received at least 1 dose of vaccine. The immunogenicity endpoints comprised the geometric mean titer (GMT) and seroconversion rate (SCR) of antigen specific immunoglobulins and wild type virus and pseudovirus neutralizing antibody titers. SCR is defined as the percentage of participants with ≥4-fold increase in titers from the baseline or from half of the lower limit of detection (LoD) if undetectable at baseline. The GMT and SCR are presented with two-sided 95% CI.

Antigen specific cellular immune responses are presented as means determined by IFN-γ ELISpot and IL-4 ELISpot.

Results

Safety. No SAE or AESI occurred at this data cut-off point. No study intervention was modified or interrupted. Occurrences of solicited AEs are summarized in FIG. 11. The most commonly reported local AEs were pain/tenderness (80.0%), while malaise/fatigue (28.9%) were the most commonly reported systemic AEs among all treatment groups. All local and systemic AEs were mild, except for one malaise/fatigue in the 25 µg dose group. No participant had fever. Solicited AEs after the first and the second dose were similar. Evaluation of safety laboratory values, ECG interpretation, and other unsolicited adverse events revealed no specific concern.

Humoral Immune Response. The humoral immunogenicity results are summarized in FIGS. 12A to 12C. As shown in FIG. 12A, binding IgG titers to S protein increased rapidly after the second dose, with seroconversion in all participants by Day 43 and 57. The GMTs peaked at Day 43 with a value of 7178.2 (95% CI: 4240.3-12151.7), 7746.1 (95% CI: 5530.2-10849.8), 11220.6 (95% CI: 8592.293-14652.84) in the 5 g, 15 g, and 25 µg dose groups, respectively. The GMT levels in the 5 µg, 15 µg, and 25 g dose groups on Day 43 ranged from 3.3 to 5.1 times the GMT of convalescent serum specimens. (2179.6, [95% CI: 1240.9-3828.4]).

As shown in FIG. 12B, no subject had detectable pseudovirus neutralizing titers ($ID_{50}$) at the lower limit of serum concentration tested (1:20 dilution) in the assay at baseline. At Day 43, the pseudovirus neutralizing titers ($ID_{50}$) showed peak GMTs of 538.5 (95% CI: 261.9-1107.0), 993.1 (95% CI: 655.0-1505.7), and 1905.8 (95% CI: 1601.7-2267.8) in the 5 µg, 15 µg, and 25 µg dose groups, respectively. All participants (100%) seroconverted after the second dose. The GMT levels in the 5 µg, 15 µg, and 25 g dose groups on Day 43 ranged from 1.25 to 4.4 times the GMT of convalescent serum specimens. (430.5, [95% CI: 274.9-674.0]).

The results of wild-type SARS-CoV-2 neutralizing antibody titers are summarized in FIG. 12C. Before vaccination, no subject had detectable wild-type virus neutralizing titers ($NT_{50}$) at the lower limit of serum concentration tested (1:8 dilution) in the assay. After the second dose, neutralizing responses were identified in serum samples from all participants in the 15 µg and 25 µg dose groups. At Day 43, the GMTs were 33.3 (95% CI: 18.5-59.9), 76.3 (95% CI: 53.7-108.3), and 167.4 (95% CI: 122.1-229.6) in the 5 µg, 15 g, and 25 µg dose groups, respectively. At Day 57, GMTs were similar in the 15 µg and 25 µg dose groups: 52.2 (95% CI: 37.9-71.8) and 81.9 (95% CI: 55.8-120.2), respectively. The GMT levels in the 5 µg, 15 µg, and 25 µg dose groups on Day 43 were 0.8, 1.8, and 3.9 times the GMT of convalescent serum specimens (42.7, [95% CI: 26.4-69.0]; titers ranged from undetected to 631.0). All participants in 15 µg and 25 µg dose groups seroconverted at Day 43 and Day 57; some were similar to the NIBSC reference serum 20/130 (281.8).

Cellular Immune Response. The results of cellular immune response are summarized in FIG. 13. All participants had minimal IFN-γ secreting T cells at baseline. By Day 57, a mean of 161.3, 85.5 and 94.9 IFN-γ secreting T cells were observed per million cells in participants vaccinated with 5 g, 15 µg, and 25 g, respectively. Before vaccination, all participants had minimal IL-4 secreting T cells. By Day 57, a mean of 24.1, 16.0 and 31.3 IL-4 secreting T cells were observed per million cells in participants vaccinated with 5 µg, 15 µg, and 25 g, respectively. The cellular immune response induced by MVC-COV1901 demonstrated substantially higher numbers of IFN-7-producing cells, suggesting a Th1-skewed immune response.

In conclusion, solicited adverse events were mostly mild and similar. No subject experienced fever. After the second dose, of the three doses evaluated, both the 15 µg and 25 µg dose elicited high neutralizing antibody responses with all participants seroconverting and a Th1-skewed T cell immune response. Therefore, 15 µg S-2P combined with CpG 1018 and aluminum hydroxide was deemed adequate to elicit a profound humoral immune response. The results also indicate that MVC-COV1901 vaccine was well tolerated and elicited robust immune responses and is suitable for further development.

Example 5 Evaluation of the Neutralizing Ability of a CpG-adjuvanted S-2P Subunit Vaccine "MVC-COV1901" Against SARS-CoV-2 Variants of Concern (VoCs)

Since the beginning of the COVID-19 pandemic, mutants have been detected periodically. A number of them, termed Variants of Concern (VoCs), were found to carry mutations in the crucial receptor-binding domain (RBD), a prime target for antibody recognition and neutralization. The most representative of these VoC, all bearing an N501Y mutation in the spike RBD, are B.1.1.1.7 (Alpha variant), B.1.351 (Bata variant), and P1 (Gamma variant). The VoCs with these mutations were found to decrease neutralization capabilities of monoclonal antibodies and vaccine-induced antibodies, and this could potentially render current therapeutics and vaccines ineffective (Garcia-Beltran et al., Cell, 184(9): 2372-2383.e9, 2021). This Example provides a study involving investigation of neutralizing ability of MVC-COV1901 vaccine against SARS-CoV-2 VoCs using sera from two sources: rat sera from animal toxicology studies and human sera from phase 1 clinical trial.

A. Neutralizing Ability of MVC-COV1901 Vaccine Against SARS-CoV-2 VoCs in Rats.

Materials and Methods

Animal studies. Crl:CD Sprague Dawley (SD) rats were obtained from BioLASCO Taiwan Co. Ltd. (Taipei, Taiwan), and studies were conducted in the Testing Facility for Biological Safety, TFBS Bioscience Inc. (New Taipei City, Taiwan). Immunization of SD rats were carried out as described in Example 2, section C. Briefly, rats were immunized three times at two weeks apart with 5, 25, or 50 µg of S-2P protein adjuvanted with 1,500 µg of CpG 1018 and 750 µg of aluminum hydroxide. The sera were harvested two weeks after the second immunization (Day 29) or two weeks after the third immunization (Day 43) and subjected to neutralization assay with pseudovirus expressing SARS-CoV-2 Wuhan wildtype (WT) or B.1.351 variant (Beta variant) spike proteins.

Pseudovirus neutralization assay. Lentivirus expressing the SARS-CoV-2 spike proteins of the Wuhan-Hu-1 wild-type strain (WT) was constructed, and the neutralization assay performed as described in Example 2, section C. Lentiviruses expressing B.1.351 variant (Beta variant) spike proteins were constructed in the same manner but with the wild-type spike protein sequence replaced with the variant sequence (GenBank Accession No. MZ314998.1).

Statistical analysis. Prism 6.01 (GraphPad Software Inc., San Diego, CA, USA) was used for statistical analysis. Two-way ANOVA with Tukey's multiple comparison test and Kruskal-Wallis with corrected Dunn's multiple comparisons test were used to calculate significance as noted in respective figure descriptions. * $p<0.05$,  $p<0.01$, * $p<0.001$, **** $p<0.0001$.

Results

MVC-COV1901-induced antibodies in rats effectively neutralized variants comparable to the wildtype. As shown in FIG. 14, at Day 29 and 43, the antibodies retained effectiveness against the B.1.351 (Beta variant), although the titers were reduced. Notably, sera sampled two weeks after the third immunization (Day 43) had higher $ID_{50}$ and $ID_{90}$ geometric mean titers (GMT) than sera sampled two weeks after the second immunization (Day 29), suggesting a trend towards improved neutralization activity against this VoC with a third immunization. The effect is especially pronounced in the low (5 µg) dose. By Day 43, all dose groups achieved similar levels of GMTs against B.1.351 at $ID_{50}$ (FIG. 14, left panel) and $ID_{90}$ (FIG. 14, right panel).

To sum up, the rat study shows that by using a three-dose regimen, we were able to induce similar levels of neutralizing titer across three-dose groups. Given that the three-dose regimen resulted in high immunogenicity against the variant, these results could be extrapolated to humans in that an extra immunization could be a strategy to increase immunity against the VoCs.

B. Neutralizing Ability of MVC-COV1901 Vaccine Against SARS-CoV-2 VoCs in Human.

Materials and Methods

Clinical trial. Forty-five (45) human subjects from the age of 20 to 49 were enrolled in a prospective, open-labeled, single-center dose-escalation phase 1 study with three separate sub-phases for participants from 20 to less 50 years of age. Each sub-phase had 15 participants. The three different dose levels employed in this clinical trial are low dose (LD; 5 µg), mid-dose (MD; 15 µg) and high dose (HD; 25 µg) of S-2P protein adjuvanted with 750 µg of CpG 1018 and 375 µg of aluminum hydroxide for phase 1a, 1b, and 1c, respectively. The vaccination schedule consisted of two doses, administered by intramuscular (IM) injection of 0.5 mL in the deltoid region of the non-dominant arm, preferably 28 days apart, on Day 1 and Day 29. On Day 57 (4 weeks after the second administration), serum samples were taken for pseudovirus neutralization assays. The clinical trial is described in greater detail in Example 4.

Pseudovirus neutralization assay. Lentivirus expressing the SARS-CoV-2 spike proteins of the Wuhan-Hu-1 wild-type strain (WT) was constructed, and the neutralization assay performed as described in Example 2, section C. Lentiviruses expressing D614G, B.1.1.7 (Alpha variant; GenBank Accession No. MZ314997.1), B.1.351 (Beta variant; GenBank Accession No. MZ314998.1), P1 (Gamma variant; GenBank Accession No. LR963075), and B.1.429 (Epsilon variant; GenBank Accession No. MW591579) spike proteins were constructed in the same manner but with the wild-type spike protein sequence replaced with the respective variant sequences.

Statistical analysis. Methods of statistical analysis were performed as described in the previous section.

Results

Human antisera from vaccination with MVC-COV1901 neutralized D614G, B.1.1.7 (Alpha), P1 (Gamma) variants, but neutralization was diminished with B.1.351 (Beta) and B.1.429 (Epsilon) variants. FIGS. 15A-C present the data from pseudovirus neutralization assays of human sera with the panel of WT, D614G, B.1.1.7 (Alpha), B.1.351 (Beta), P1 (Gamma), and B.1.429 (Epsilon) variants. Although the titers of neutralizing antibodies of all groups (LD, MD, and HD groups) against D614G and B.1.1.7 (Alpha variant) dropped compared to that against WT (FIGS. 15A-C), the reductions were not statistically significant. However, when comparing B.1.351 (Beta variant) with the WT, the titers of neutralizing antibodies decreased significantly in all groups (LD, MD, and HD groups). In contrast, titers of neutralizing antibodies of all groups (LD, MD, and HD groups) against P1 (Gamma variant) are higher than that against WT. Although when comparing B.1.429 (Epsilon variant) with the WT, the titers of neutralizing antibodies decreased significantly in LD and MD groups (FIGS. 15A-B), there was no significant difference in titers of neutralizing antibodies against B.1.429 (Epsilon variant) in HD group (FIG. 15C). A dose-dependent effect could be observed when plotting each dose group's neutralizing titers against the variants (FIGS. 15A-C). The neutralizing titers against B.1.351 (Beta), P1 (Gamma), and B.1.429 (Epsilon) variants could be increased by using a higher dose of antigen.

In conclusion, vaccinated phase 1 human subjects showed more reduced but still appreciable neutralization abilities against the B.1.351 (Beta), P1 (Gamma), and B.1.429 (Epsilon) variants at $ID_{90}$, especially at higher doses. The results indicate that two doses of MVC-COV1901 were able to elicit neutralizing antibodies against SARS-CoV-2 variants in a dose-dependent manner.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. An immunogenic composition against a severe acute respiratory syndrome coronavirus 2 (SARS-CoV-2), comprising an antigenic recombinant protein and an adjuvant consisting of aluminum hydroxide and an unmethylated cytosine-phosphate-guanosine (CpG) motif consisting of a synthetic oligodeoxynucleotide (ODN) of SEQ ID NO: 8, wherein the antigenic recombinant protein substantially consists of residues 14-1208 of SARS-CoV-2 S protein with proline substitutions at residues 986 and 987 and a "GSAS" substitution at residues 682-685 and a C-terminal T4 fibritin trimerization domain consisting of an amino acid sequence of SEQ ID NO: 2.

2. The immunogenic composition of claim 1, wherein the residues 14-1208 of SARS-CoV-2 S protein with proline substitutions at residues 986 and 987 and a "GSAS" substitution at residues 682-685 comprise an amino acid sequence of SEQ ID NO: 1 or the amino acid sequence at least 90%, 95%, 96%, 97%, 98%, or 99% to SEQ ID NO: 1.

3. The immunogenic composition of claim 1, wherein the antigenic recombinant protein comprises an amino acid sequence of SEQ ID NO: 5 or 6 or the amino acid sequence at least 90%, 95%, 96%, 97%, 98%, or 99% to SEQ ID NO: 5 or 6.

4. The immunogenic composition of claim 1, wherein a 0.5 ml dose of the immunogenic composition comprises from about 250 to about 500 μg $Al^{3+}$, or about 375 μg $Al^{3+}$.

5. The immunogenic composition of claim 1, wherein a 0.5 ml dose of the immunogenic composition comprises from about 750 to about 3000 μg of the synthetic oligodeoxynucleotide, or wherein the immunogenic composition comprises about 750 μg, about 1500 μg, or about 3000 μg of the synthetic oligodeoxynucleotide.

6. A method for eliciting an immune response against a severe acute respiratory syndrome coronavirus 2 (SARS-CoV-2) in a subject in need thereof, comprising administering to the subject an effective amount of an immunogenic composition comprising an antigenic recombinant protein and an adjuvant consisting of aluminum hydroxide and an unmethylated cytosine-phosphate-guanosine (CpG) motif consisting of a synthetic oligodeoxynucleotide (ODN) of SEQ ID NO: 8, wherein the antigenic recombinant protein substantially consists of residues 14-1208 of SARS-CoV-2 S protein with proline substitutions at residues 986 and 987 and a "GSAS" substitution at residues 682-685 and a C-terminal T4 fibritin trimerization domain consisting of an amino acid sequence of SEQ ID NO: 2.

7. The method of claim 6, wherein the residues 14-1208 of SARS-CoV-2 S protein with proline substitutions at residues 986 and 987 and a "GSAS" substitution at residues 682-685 comprise an amino acid sequence of SEQ ID NO: 1 or the amino acid sequence at least 90%, 95%, 96%, 97%, 98%, or 99% to SEQ ID NO: 1.

8. The method of claim 6, wherein the antigenic recombinant protein comprises an amino acid sequence of SEQ ID NO: 5 or 6 or the amino acid sequence at least 90%, 95% 96%, 97%, 98%, or 99% to SEQ ID NO: 5 or 6.

9. The method of claim 6, wherein a 0.5 ml dose of the immunogenic composition comprises from about 250 to about 500 μg $Al^{3+}$, or about 375 μg $Al^{3+}$.

10. The method of claim 6, wherein a 0.5 ml dose of the immunogenic composition comprises from about 750 to about 3000 μg of the synthetic oligodeoxynucleotide, or wherein the immunogenic composition comprises about 750 μg, about 1500 μg, or about 3000 μg of the synthetic oligodeoxynucleotide.

11. The method of claim 6, wherein the immune response comprises production of neutralizing antibodies against SARS-CoV-2 and Th1-skewed immune response.

12. The method of claim 6, wherein the immunogenic composition is administered by intramuscular injection.

13. A method for protecting a subject in need thereof from infection with severe acute respiratory syndrome coronavirus 2 (SARS-CoV-2) or preventing the subject in need thereof from contracting COVID-19 disease, comprising administering to the subject an effective amount of the immunogenic composition of claim 1.

14. The method of claim 13, wherein the immunogenic composition is administered by intramuscular injection.

* * * * *